(12) United States Patent
LeClerc et al.

(10) Patent No.: US 10,004,794 B2
(45) Date of Patent: *Jun. 26, 2018

(54) VECTORS FOR MOLECULE DELIVERY TO CD11B EXPRESSING CELLS

(71) Applicants: INSTITUT PASTEUR, Paris (FR); CENTRE NATIONAL DE LA RECHERCHE SCIENTIFIQUE, Paris (FR)

(72) Inventors: Claude LeClerc, Paris (FR); Pierre Guermonprez, Cachan (FR); Daniel Ladant, Cachan (FR); Nicole Guiso, Paris (FR); Nadia Khelef, Paris (FR); Cecile Bauche, Paris (FR); Catherine Fayolle, Epinay sur Orge (FR); Mohammed El-Azami El-Idrissi, Paris (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/177,029

(22) Filed: Jun. 8, 2016

(65) Prior Publication Data

US 2016/0375119 A1 Dec. 29, 2016

Related U.S. Application Data

(60) Continuation of application No. 13/169,605, filed on Jun. 27, 2011, now Pat. No. 9,370,564, which is a continuation of application No. 11/098,404, filed on Apr. 5, 2005, which is a division of application No. 10/387,486, filed on Mar. 14, 2003, which is a continuation of application No. PCT/EP01/11315, filed on Sep. 14, 2001.

(30) Foreign Application Priority Data

Sep. 15, 2000 (EP) .................................. 00402562

(51) Int. Cl.
| | |
|---|---|
| A61K 39/02 | (2006.01) |
| A61K 39/385 | (2006.01) |
| C12N 9/88 | (2006.01) |
| C12N 15/85 | (2006.01) |
| A61K 47/64 | (2017.01) |
| A61K 39/00 | (2006.01) |

(52) U.S. Cl.
CPC .......... *A61K 39/099* (2013.01); *A61K 39/385* (2013.01); *A61K 47/646* (2017.08); *C12N 9/88* (2013.01); *C12N 15/85* (2013.01); *C12Y 406/01001* (2013.01); *A61K 2039/57* (2013.01); *A61K 2039/6037* (2013.01)

(58) Field of Classification Search
None
See application file for complete search history.

(56) References Cited

U.S. PATENT DOCUMENTS

| | | | |
|---|---|---|---|
| 5,182,211 A | 1/1993 | Girard et al. | |
| 5,183,745 A | 2/1993 | Danchin et al. | |
| 5,312,902 A | 5/1994 | Montagnier et al. | |
| 5,403,484 A | 4/1995 | Ladner | |
| 5,503,829 A | 4/1996 | Ladant et al. | |
| 5,679,784 A | 10/1997 | Ladant et al. | |
| 5,821,122 A | 10/1998 | Guilloux et al. | |
| 5,935,580 A * | 8/1999 | Ladant ................. | C07K 14/005 424/184.1 |
| 5,952,303 A | 9/1999 | Bornstein et al. | |
| 6,333,154 B1 * | 12/2001 | Ladant .................. | C12Q 1/025 435/29 |
| 6,500,641 B1 | 12/2002 | Chen et al. | |
| 6,673,914 B1 | 1/2004 | Hoon | |
| 7,906,123 B1 * | 3/2011 | Leclerc .................... | C12N 9/88 424/184.1 |
| 8,017,132 B2 * | 9/2011 | Sebo ........................ | C12N 9/88 424/185.1 |
| 8,628,779 B2 * | 1/2014 | Preville ................ | C07K 14/005 424/185.1 |
| 9,370,564 B2 * | 6/2016 | LeClerc ............... | A61K 39/385 |
| 9,410,139 B2 * | 8/2016 | Dadaglio ............. | A61K 38/164 |
| 2004/0001867 A1 | 1/2004 | Leclerc et al. | |

(Continued)

FOREIGN PATENT DOCUMENTS

| | | |
|---|---|---|
| EP | 0406857 A1 | 1/1991 |
| EP | 1188446 A1 | 3/2002 |

(Continued)

OTHER PUBLICATIONS

Ladant et al. 1999 (Bordetella pertussis adenylate cyclase: a toxin with multiple talents; Trends in Microbiology 7(4):172-176).*

Benz et al. 1994 (Adenylate Cyclase Toxin CyaA) of Bordetella pertussis; The Journal of Biological Chemistry 269(44): 27231-27239).*

Masin, J., et al. "Acylation of Lysine 860 Allows Tight Binding and Cytotoxicity of Bordetella Adenylate Cyclase on 001 lb-Expressing Cells" Biochemistry, 44:12759-12766 (2005).

(Continued)

*Primary Examiner* — Mary Maille Lyons
(74) *Attorney, Agent, or Firm* — Arrigo, Lee, Guttman & Mouta-Bellum LLP

(57) ABSTRACT

The invention relates to a novel use of a *Bordetella* adenyl-cyclase toxin in the manufacturing of vectors for targeting in vivo a molecule of interest, specifically to CD11b expressing cells. The invention also relates to an immunogenic composition that primes immune responses, to pharmaceutical compositions and to a new vector for molecule delivery to CD11b expressing cells.

16 Claims, 25 Drawing Sheets

(56) References Cited

U.S. PATENT DOCUMENTS

Figure 1A:
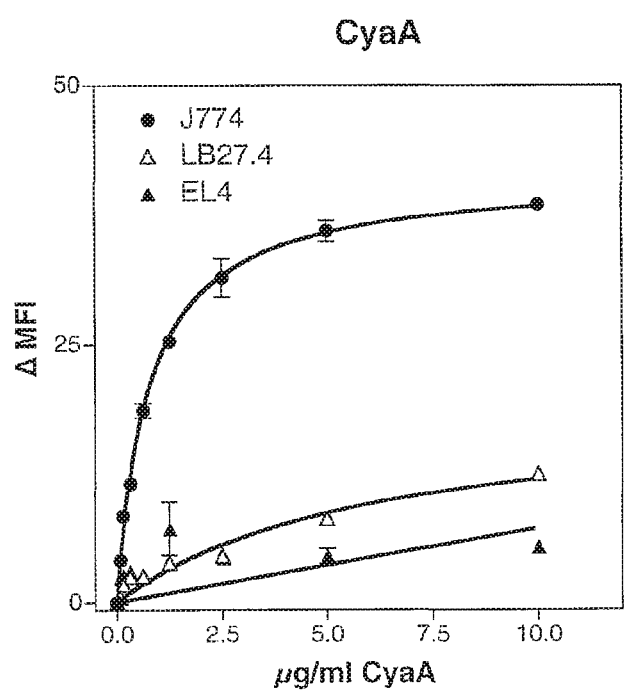
Figure 1B:
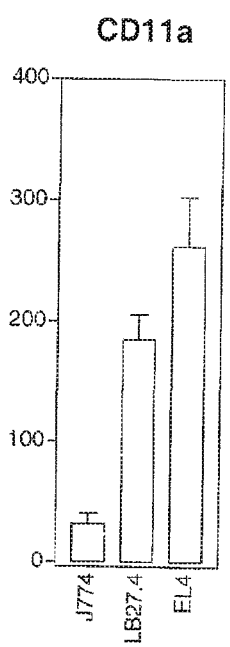
Figure 1C:
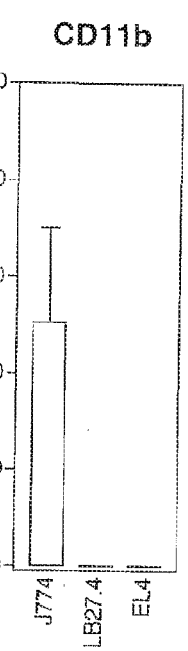
Figure 1D:
Figure 1E:
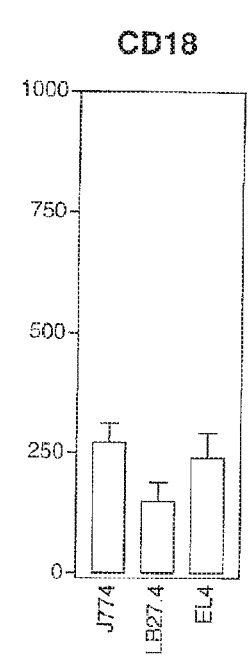

| | | |
|---|---|---|
| 2005/0271679 A1 | 12/2005 | Dadaglio et al. |
| 2007/0026022 A1 | 2/2007 | Dadaglio et al. |
| 2007/0072266 A1 | 3/2007 | Preville et al. |
| 2009/0117143 A1 | 5/2009 | Dadaglio et al. |
| 2010/0150999 A1 | 6/2010 | Leclerc et al. |

FOREIGN PATENT DOCUMENTS

| | | |
|---|---|---|
| EP | 1576967 A1 | 9/2005 |
| WO | 92/00099 | 1/1992 |
| WO | 93/21324 | 10/1993 |
| WO | 96/40123 A1 | 12/1996 |
| WO | 01/29220 A2 | 4/2001 |
| WO | 02/22169 A2 | 3/2002 |
| WO | 2004/113372 A1 | 12/2004 |
| WO | 2005/035557 A2 | 4/2005 |
| WO | 2005/053738 A1 | 6/2005 |
| WO | 2005/089792 A1 | 9/2005 |

OTHER PUBLICATIONS

"Method for introducing a peptide into the cytosol; by linking to a toxin to translocate the peptide to the cytosol and presentation at the cell surface as a Class I WIC antigen; recombinant vaccine preparation" Vaccine, 10:638 (1992).

Mikayama et al., "Molecular cloning and functional expression of a cDNA encoding glycosylation-inhibiting factor" Proc. Nat!, Acad. Sci. USA, 90:10056-10060 (1993).

Moore, M. et al., "Introduction of Soluble Protein into the Class I Pathway of Antigen Processing and Presentation" Cell, 54:777-785 (1988).

Norley, S. et al., "Vaccination against HIV" immunobiol., 4:193-207 (1992).

Office Action dated Jan. 14, 2010 in U.S. Appl. No. 11/517,313.

Office Action dated Oct. 14, 2010 n U.S. Appl. No. 11/778,267.

Osicka at al., "Delivery of CD8+ T-cell epitopes into major histocompatibility complex class I antigen presentation pathway by Bordetella pertussis adenylate cyclase: delineation of cell invasive structures and permissive insertion sites" Infect. 1m/run., 68:247-256 (2000).

Parkhill, J. et al., "Bifunctional Hemolysin-Adenylate Cyclase Precursor [Bordetella Bronchiseptica RB50]" Database EMBL Accession No. CAE30822, Jul. 29, 2008 (2 pages).

Parkhill, J. et al., "Bifunctional Fiernolysin-Adenylate Cyclase Precursor [Bordetella Parapertussis 12822]" Database EMBL Accession No. NP 882677, Jul. 21, 2008 (2 pages).

Parkhill, J. et al., "Bordetella parapertussis 12822, complete genome," GenBank Accession NC 002928, Aug. 12, 2003, pp. 1 and 85 of 1042.

Parkhill, J., et al., "Comparative analysis of the genome sequences of Bordetella pertussis, Bordetella parapertLissis and Bordetella bronchiseptica" Nat. Genet., 35 (1):32-40 (2003).

Pashine, A. et al., "Targeting the innate immune response with improved vaccine adjuvants" Nat. Med. Suppl., 11(4):S63-S68 (2005).

Preville, X. et al., "Eradication of Established Tumors by Vaccination With Recombinant Bordetella pertussis Adenylate Cyclase Carrying the Human Papillornavirus 16 E7 Oncoprotein" Cancer Res., 65(2):641-649 (2005).

Renkvist et al., "A Listing of Human Tumor Antigens Recognized by T Cells" Cancer Immunology and Immunotherapy, 50(1):3-15 (2001).

Rodeck et al., "Monoclonal Antibody 425 Inhibits Growth Stimulation of Carcinoma Cells by Exogenous EGF and Tumor-Derived EGF/TGF-a" J. Cell Biechem,, 44(2):69-79 (Oct. 1990).

Rudinger et al., "Characteristics of the amino acids as components of a peptide hormone sequence" in Peptide Hormones. J. A. Parsons (ed.), University Park Press, Jun. 1976; pp. 5-7.

Schlect, G. et al., Antigen Targeting to CD11 b Allows Efficient Presentation of CD4 and CD8+ Epitopes and In Vivo Thl-Polarized T Cell Priming J. irritnunal., 173:6089-6097 (2004).

Schulz, M. et al., "Major histocompatibility complex-dependent T cell opitopes of lymphocytic choriomeningitis virus nucleoprotein and their protective capacity against viral disease" Eur. J. 1171rflUt101., 19:1657-1667 (1989).

Sebo et al., "Cell-invasive activity of epitope-tagged adenylate cyclase of Bercleteila pertussis allows in vitro presentation of a foreign epitope to CD8' cytotoxic T cells" Infect. Immun., 63:3851-3857 (1995).

Sebo et al., "High-level synthesis of active adenylate cyclase toxin of Bordetella pertussis in a reconstructed *Eschefichia coil* system" Gene, 104:19-24 (1991).

Sebo et al., "In vivo induction of OIL responses by recombinant adenylate cyclase of Bordetella pertussis carrying multiple copies of a viral CDS—T-cell epitope" FE-:MS immune/. Microbiol., 26(2):167-173 (1999).

Skipper et al., "An HLA-A2-Restricted Tyrosinase Antigen on Melanoma Cells Results from Postransiational Modification and Suggests a Novel Pathway for Processing of Membrane Proteins" J. Exp. Med., 183(2):527-534 (1996).

Skolnick at al., "From genes to protein structure and function: novel applications of computational approaches in the genomic era" Trends in Biotech, 18(1):34-39 (2000).

Stenmark, H. et al., "Peptides fused to the amino-terminal end of diphtheria toxin are transiocated to the cytosol" J. Cell. Biol., 113(5):1025-1032 (1991).

Takahashi, H. et al., "An immunodominant epitope of the human immunodeficiency virus envelope glycoprotein gp160 recognized by class I major histocompatibility complex molecule-restricted murine cytotoxic I lymphocytes" Proc. Natl. Acad. Sci. USA, 85:3105-3109 (1988).

Ta, J.P. et al:, "Vaccine engineering: Enhancement of immunogenecity of synthetic peptide vaccines related to hepatitis in chemically defined models consisting of T- and B-cell epitopes" Proc. Natl. Acad. Sci USA, 86:9084-9088 (1989).

U.S. Appl. No. 10/994,204: Decision on Appeal, Jan. 25, 2010.

Vierboom, M.P.M. et al,, "Cyclophosphamide Enhances Anti-Tumor Effect of Wild-Type p53-Specific CTL" Int. J. Cancer, 87:253-260 (2000).

Welch, R,A., "Pore-forming cytolysins of Gram-negative bacteria" Mot. Microbiol., 5(3):521-528 (1991).

Creighton, Thomas E., Protein Structure: A Practical Approach, 1989, pp. 184-186.

Creighton, Thomas E., Proteins: Structures and Molecular properties, 1984, pp. 314-315.

Dadaglio et al., Infection and Immunity, Jul. 2000, pp. 3567-3872.

Fayolle et al., The Journal of immunology, vol. 162, No. 7. pp. 4147-4162.

Glaser et al., The EMBO Journal, vol. 8, No. 3, 1989, pp. 967-972.

Goyard et al., Zbl. Bakt. 278, pp. 326-333.

Ladant et al., The Journal of Biological Chemistry, vol. 257, No. 4, pp. 2244-2250.

Nosoh, Y. et al., in Protein Stability and Stabilization through protein Engineering, 1991, Chapter 7, p. 197, second paragraph.

Ladant et al. 1992 (Insertional Mutagenesis of Bordetella pertussis Adenylate Cyclase; The Journal of Biological Chemistry 267(4)2244-2250).

El-Azami-El-Idrissi et al. 2003 (Interaction of Bordetella pertussis Adenylate Cyclase with CD11b/CD18; Journal of Biological Chemistry; 278(40)28514-38521).

Baca et al. 1995 (Chemical ligation of cysteine-containing peptides: synthesis of a 22 kDa Tethered Dimer of HIV-1 Protease).

Brosnan et al. 2006 (The Sulfur-Containing Amino Acids: An Overview; The Journal of Nutrition; Supplement 1636-1639; see abstract).

Greenspan et al. 1999 (Defining epitopes: Its not as easy as it seems; Nature Biotechnology, 17:936-937).

Ladant and Ullman 1999 (Bordetella pertussis adenlyate cyclase: a toxin with multiple talents; Trends in Microbiology, 7(4), 172-176.

(56) References Cited

OTHER PUBLICATIONS

Wout et al. 1992 (Role of carbohydrate recognition domains of pertussis toxin in adherence of Bordetella pertussis to human macrophages; Infection and immunity, 60:3330-3308).
Aichele et al., "Antiviral Cytotoxic I Cell Response Induced by In Vivo Priming with a Free Synthetic Peptide" J. Exp. Med., 171(5):1815-20 (1990).
Alberts et al. (eds.), Definition of "Antigen" and "Antigenic determinant (epitope)", in Molecular Eigji_Dgf the Cell. Fourth Edition, Garland Science, 2002, p. G:3.
Basar, I. et al., "The Conserved Lysine 860 in the Additional Fatty-acylation Site of Bordetella pertussis Adenylate Cyclase Is Crucial for Toxin Function Independently of Its Acylation Status",J, Biol. Chem., 274(16):10777-10783 (1999).
Basler, M. et al., "Segments Crucial for Membrane Translocation and Pore-forming Activity of Bordetella Adenylate Cyclase Toxin" J. Biol. Chem . . . 282(17):12419-12429 (2007).
Basler, M., et al., Pore-Forming and Enzymatic Activities of Bordetella pertussis Adenylate Cyclase Toxin Synergize in Promoting Lysis of Monocytes Infection and Immunity, 74(4):2207-2214(2006).
Baur, S. et al., "Identific n of H-2Kb Binding and Immunogenic Peptides from Human Papilloma Virus Tumour Antigens E6 and E7" Scand. J. Immunol., 42:317-323 (1995).
Berzofsky et al., "Epitopes of HIV and Sly. Host Responses" AIDS Res. Human Retroviruses, 7(2):144-147 (1991).
Betsou, F. et al., "Bordetella bronchiseptica adenylate cyclase-hemolysin (cya) gene, complete cds" GenBank Accession U22953, Mar. 23, 1995 (3 pages).
Betsou, F. et al., "Cloning and sequence of the Bordetella bronchiseptica adenylate cyclase-hernolysin-encoding gene: comparison with the Bordetella pertussis gene" Gene, 162:165-166 (1995).
Bowie, J.V. et al., "Deciphering the Message in Protein Sequences: Tolerance to Amino Acid Substitutions" Science, 247:1306-1310 (1990).
Casselll, D. et al. "Linked Recognition of Helper and Cytotoxic Antigenic Determinants for the Generation of Cytotoxic T Lymphocytes" Ann. N.Y. Acad, Sci, pp. 51-60(1991).
Chothia et al., "The relation between the divergence of sequence and structure in proteins" EMBO J.,5(4):823-826 (1986).
Chung et al., "Generation of tumor-specific cytotoxic T lymphocyte and prolongation of the survival of tumor-bearing mice using interleukin-18-secreting fibroblasts loaded with an epitope peptide" Vaccine, 22:2547-2557 (2004).
Clustal 2.0,10 sequence alignment of SEC) ID Nal with NP 882677. 1, performed Jul. 22, 2010 (2 pages).
Dadaglio et al., "Recombinant Adenylate Cyclase Toxin of Bordetella pertussis Induces Cytotoxic T Lymphocyte Responses Against HLA0201-Restricted Melanoma Epitopes" International Immunology, 15(2):1423-1430 (2003).
Danchin , "cyaA [Bordetella pertussis]" Database E-NBL Accession No. CAA3241 i, Apr. 18, 2005 (1 page).
Darnell et al., Molecular Cell Biology. Scientific American Books, 1986; pp. 108-109 and 102 1105.
Donato, G.M. et al,, "Adenylate Cyclase Toxin [Bordetella Hinzii]" Database EMBL Accession No. AAZ57194, Nov. 4, 2005 (1 page).
Donato, G.M. et al., "Bordetella hinzii strain BC-306 adenylate cyclase toxin (cyaA) gene, complete cds," GenBank Accession DQ102773, Nov. 4, 2005 (3 pages).
Donato, G.M. et al., "Bordetella hinzii strain LMG 13501 adenylate cyclase toxin (cyaA) gene, complete cds," GenBank Accession 0Q007078, Nov. 4, 2005 (3 pages).
Donato, G.M., et al., "Adenylate cyclase toxin (ACT) from Bordetella hinzii: characterization and differences from ACT of Bordetella pertussis" J. BacterioL, 187(22):7579-7588 (2005).
Drexler et al., "Modified Vaccinia Virus Ankara for Delivery of Human Tyrosinase as Melanoma-associated Antigen: Induction of Tyrosinase- and Melanoma-specific Human Leukocyte Antigen A*0201-restricted Cytotoxic T Cells in vitro and in Vivo" Cancer Res., 59:4955-4963 (Oct. 1999).
European Patent Application No. 00402562: European Search Report, dated Jul. 2, 2001 (4 pages).
European Patent Application No. 06291393: Extended Search Report, dated Feb. 8, 2007 (5 pages).
European Patent Application No. 09155929: Extended Search Report, dated May 13, 2009 (8 pages).
Fayolle et al., "Bordetella pertussis adenylate cyclase delivers chemically coupled CD8+ T-cell epitopes to dendritic cells and elicits OIL in vivo" Vaccine, 23.604-614 (2004).
Fayolle et al., "Delivery of multiple epitopes by recombinant detoxified adenylate cyclase of Bordetella pertussis induces protective antiviral immunity" J. Virol., 75(16):7330-7338 (2001).
Fayolle et al., "In Vivo Induction of Cytotoxic T Cell Response by a Free Synthetic Peptide Requires CD4+ T Cell Help" J. Iminunoi., 147:4069-4073 (1991).
Fier, R. et al., "Third Activity of Bordetella Adenylate Cyclase (AC) Toxin-Hemolysin, Membrane Translocation of AC Domain Polypeptide Promotes Calcium Influx Into CD11b' Monocytes Independently of the Catalytic and Hemolytic Activities" J. Biol. Chem., 282(5)2808-2820 (2007).
Forestier et al., "Identification of RTX Toxin Target Cell Specificity Domains by Use of Hybrid Genes" Infect. Immun.,59(11):4212-4220 (1991).
Glaser et al., The calrnodulin-sensitive adenylate cyclase of Bordetella pertussis: cloning and expression in *Escherichia coil* Malec. Microbici.,2(1):19-30 (1988).
Gmira, S. et al., "Characterization of recombinant Bordetella pertussis adenylate cyclase toxins carrying passenger proteins" Research in Microbiology, 152(10):889-900 (Dec. 2001).
Goyard, S. et al., "Analysis of Bordetella pertussis cya operon regulation by use of cya-lac fusions" FEMS Microbiol. Lett., 77:251-256 (1991).
Greenspan et al., "Defining epitopes: Its not as easy as it seems" Nat. Biotechnoi., 7:936-937 (1999).
Guermonprez et al., "Direct delivery of the Bordetelia pertussis adenylate cyclase toxin to the MI-1C class I antigen presentation pathway" J. Immunoi., 162(4):1910-1916 (1999).
Guermonprez et al., The adenylate cyclase toxin of Bordetella pertussis binds to target cells via the ar,432 integrin (CD11b/CD181, J. Exp. Med.,193(9):1035-1044 (2001).
Guermonprez, P. et al., "Bordetella pertussis Adenylate Cyclase Toxin: A Vehicle to Deliver 008-Positive T-Cell Epitopes Into Antigen-Presenting Cells" Methods in Enzymology, 326:527-542 (2000).
Guermonprez, P. et al., "Les toxines bacteriennes recombinantes: de nouveaux vecteurs pour la vaccination?" Medecine/Sciences,16(5):653-662 (May 2000), English summary, p. 662.
Hanski, E., "Invasive adenylate cyciase toxin of Bordeteiia pertussis" 1785, 4:459-463 (1989).
Hart et al., "Priming of anti-human immunodeficiency virus (HIV) 0D84 cytotoxic T cells ill vivo by carrier-free HIV synthetic peptides" Proc. Natl. Acad. Sci. USA, 88:9448-9452 (1991).
Heveker, N. et al., "Characterization of mutant Bordetella pertussis adenylate cyclase toxins with reduced affinity for calmodulin. Implications for the mechanism of toxin entry into target cells" Eur, J. Biochem., 243(3):643-649 (Feb. 1997).
International Search Report from PCT/EP01/11315, dated Aug. 26, 2002.
International Search Report from PCT/EP2004/014086, dated Apr. 19, 2005.
International Search Report from PCT/IB2007/003093 dated Jul. 16, 2007.
International Search Report from PCT/EP2010/053795, dated Jul. 5, 2010.
Ishibashi et al., "Bordetella pertussis Filamentous Hemaglutinin Interacts with a Leukocyte signal Transduction Complex and Stimulates Bacterial Adherence to Monocyte CR3 (CD11b/0018)" J. Exp. Med., 180:1225-1233 (1994).

(56) References Cited

OTHER PUBLICATIONS

Kather, A. et al. "Identification of a Naturally Processed HLA-A0201 HPV18 E7 T Cell Epitope by Tumor Cell Mediated in Vitro Vaccination" int. J. Cancer, 104:345-353 (2003).

Ladant, D. et al., "Bordetella pertussis adenylate cyclase: A toxin with multiple talents" Trends in Microbiology, 7(4):172-176 (Apr. 1999).

LeClerc et al., "Identification of a T-Cell Epitope Adjacent to Neutra zation Antigenic Site 1 of Poliovirus Type 1" J. Virol., 65:711-718 (1991).

LeClerc et al., "The Cellular Location of a Foreign B Cell Epitope Expressed by Recombinant Bacteria Determines Its T Cell-Independent or T Cell-Dependent Characteristics" J. immune!,, 147:3545-3552 (1991).

\* cited by examiner

µg/ml CyaA

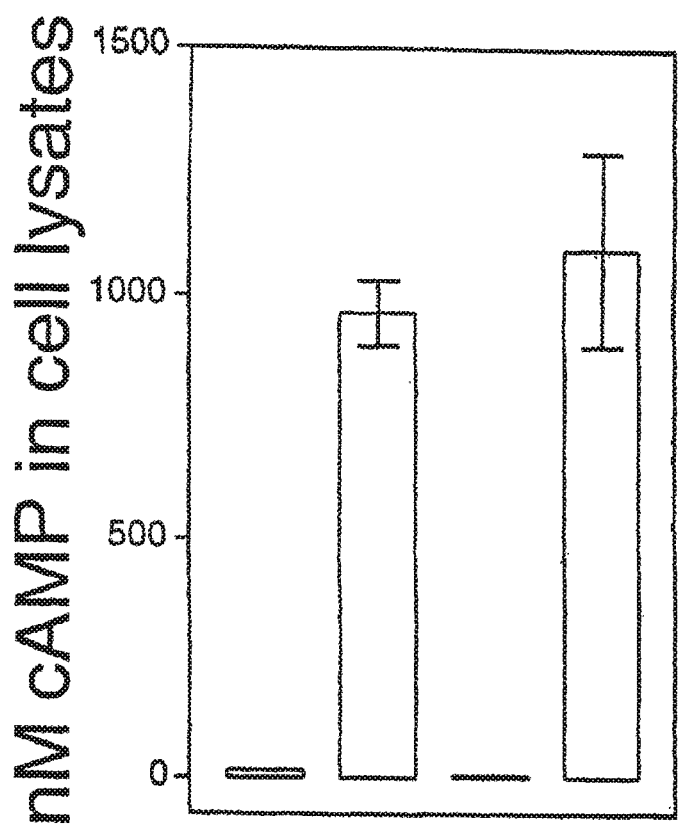

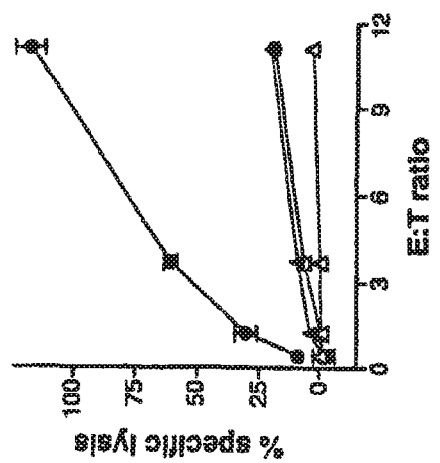
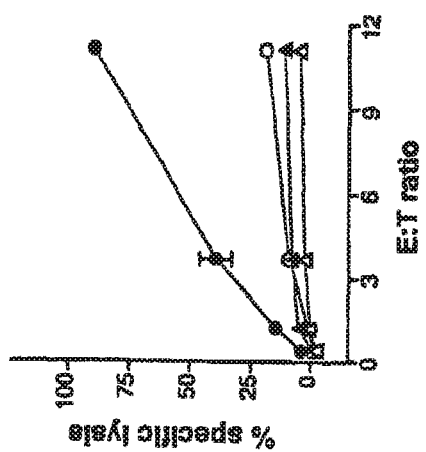
FIG. 6B
FIG. 6A

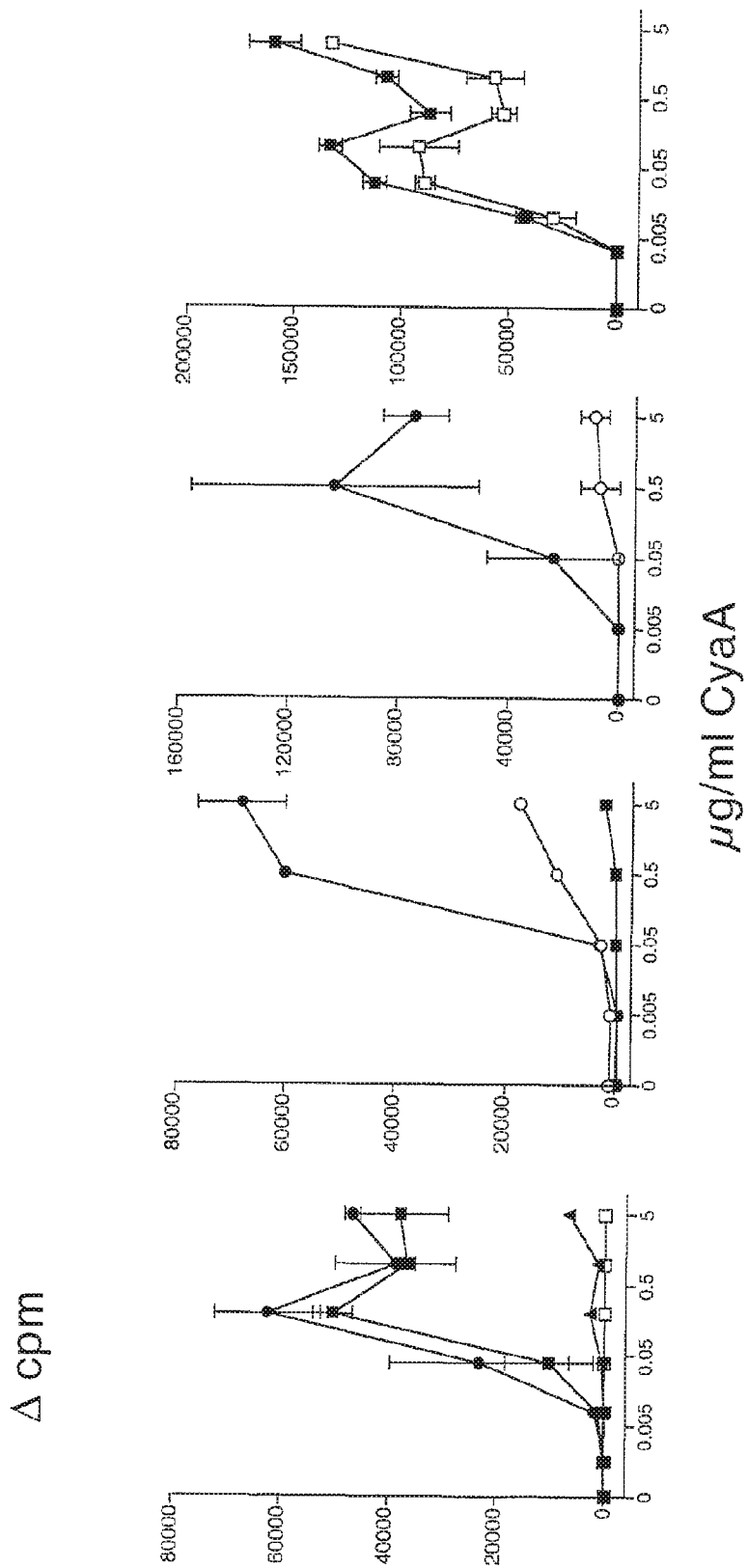

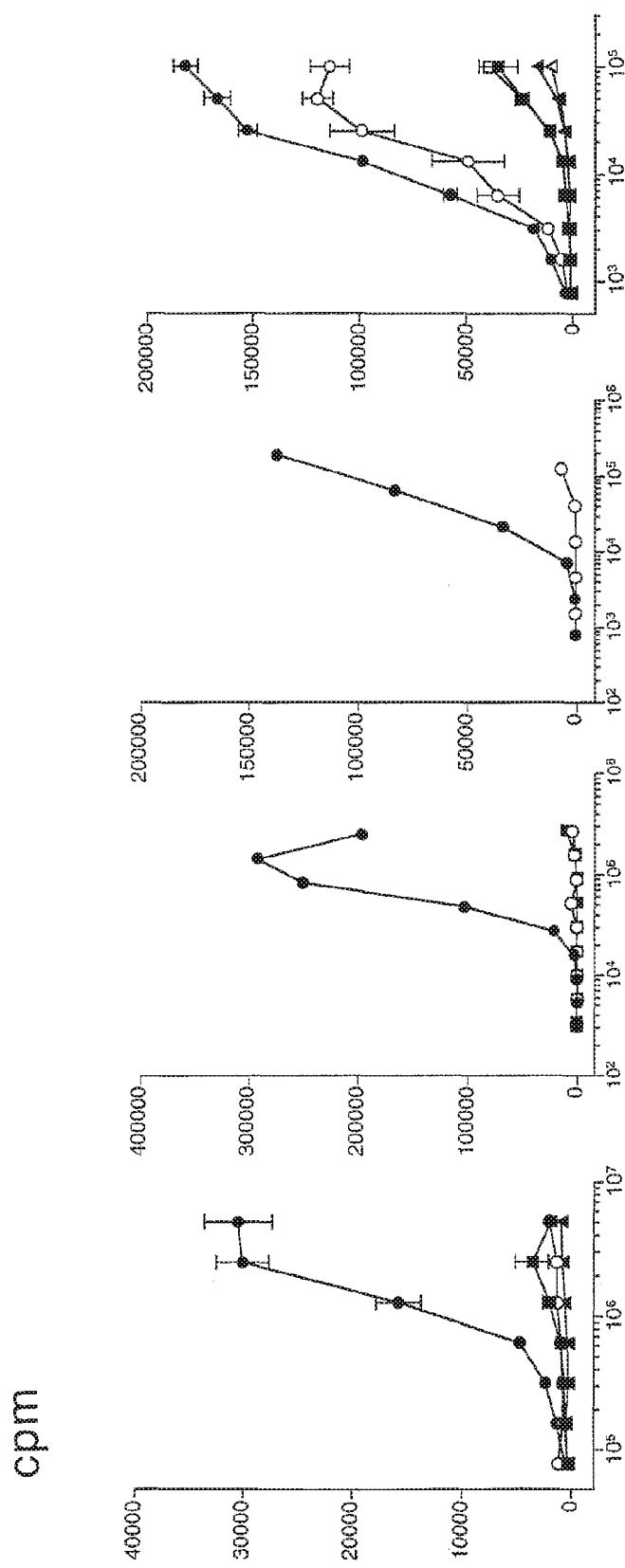

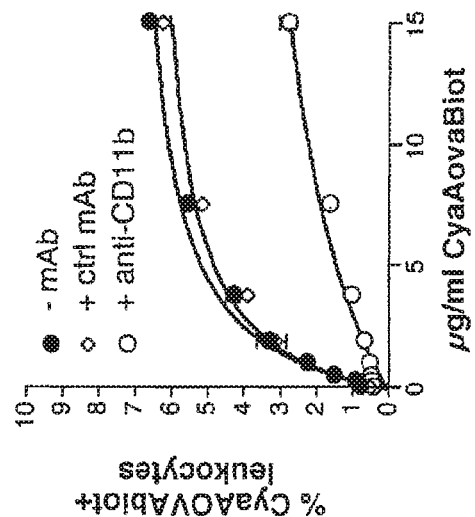
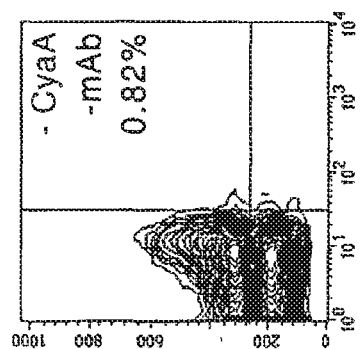
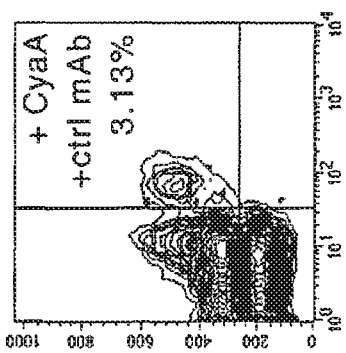
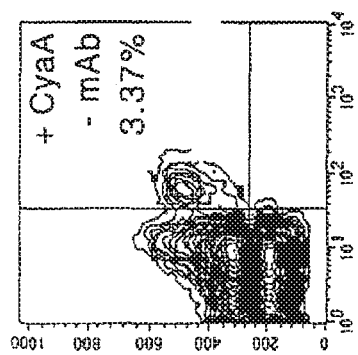
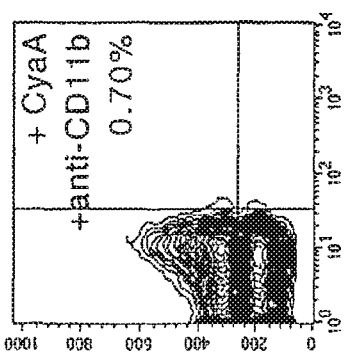

11c+CD8α+

11c+CD8α-

11c-CD8α+

11c-CD8α-

CyaAOVA      CD11b

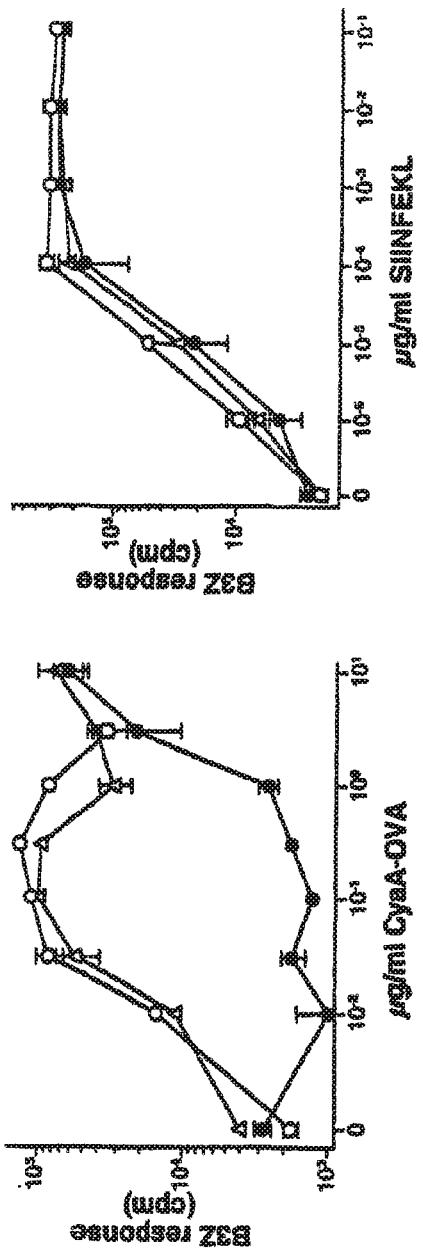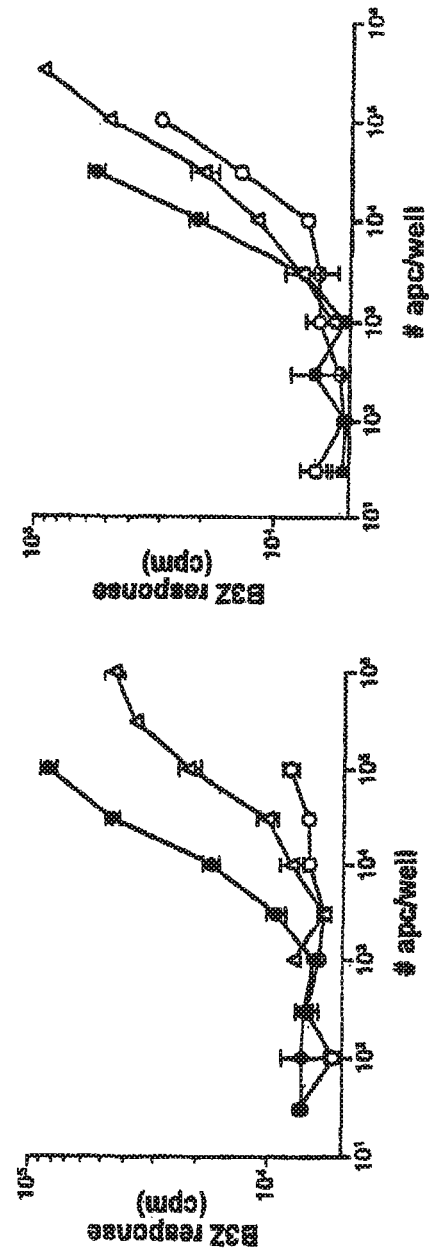

1 - Insertion of Cys in CyaA (devoid of Cys residue)
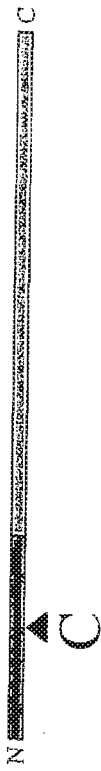
2 - Chemical Synthesis of Cys(NPys)-peptide

VECTORS FOR MOLECULE DELIVERY TO CD11B EXPRESSING CELLS

BACKGROUND OF THE INVENTION

The invention relates to a novel use of a *Bordetella* adenylcyclase toxin in the manufacturing of vectors for targeting in vivo a molecule of interest, specifically to CD11b expressing cells. The invention also relates to an immunogenic composition that primes immune responses, to pharmaceutical compositions and a new vector for molecule delivery to CD11b expressing cells.

*Bordetella pertussis*, the causative agent of whooping cough, secretes several toxins including the well-known pertussis toxin (PT) and the adenylate cyclase toxin (CyaA) or also adenylcyclase. CyaA is a critical virulence factor of *B. pertussis* in the murine respiratory model that is required for the early steps of lung colonization. Indeed, genetic deletion of this toxin dramatically decreases the pathological effects of *B. pertussis* infection, reducing the number of bacteria recovered from the lung and almost abolishing the inflammatory cell recruitment and the lung lesions observed after infection [Weiss et al., 1984; Weiss et al., 1989; Gross et al., 1992; Khelef et al., 1992; Khelef et al., 1994; Gueirard et al., 1998]. Moreover, CyaA is an antigen protective against *B. pertussis* infection in the murine respiratory model [Guiso et al., 1989; Guiso et al., 1991].

Originally discovered by Hewlett et al in *B. pertussis* culture supernatants [Hewlett et al., 1976], the adenylcyclase was later found to be activated by the eukaryotic calmodulin [Wolff et al., 1980]. This striking feature quickly found a rationale when it was shown by Confer and Eaton that the adenylcyclase could enter into eukaryotic cells where, upon activation by calmodulin, it could trigger a large increase in cAMP within these target cells [Confer et al., 1982].

Adenylcyclase is encoded by the cyaA gene, and its expression, like that of other virulence genes of *B. pertussis*, is coordinately regulated by environmental signals. The cyaA gene is part of an operon that also contains genes cya B, D and E, that are required for CyaA secretion [Ladant et al., 1999].

The CyaA toxin is a bifunctional protein of 1706 residues that is made of a N-terminal catalytic domain of 400 amino acids and a C-terminal part of 1306 residues which is responsible for the binding of the toxin to target cell membrane and the subsequent delivery of the catalytic moiety into the cell cytosol [Sakamoto et al., 1992] [Ladant et al., 1999]. This part also exhibits a weak hemolytic activity due to its ability to form cation-selective channels in biological membranes [Benz et al., 1994] [Gray et al., 1998]. This region is homologous to *Escherichia coli* hemolysin and other members of the RTX (Repeat in ToXin) family of bacterial toxins. In particular, it contains a series of glycine and aspartate-rich nonapeptide repeats that are involved in calcium binding [Rose et al., 1995] [Coote et al., 1992].

The CyaA polypeptide is synthesized as an inactive protoxin that is converted to an active toxin by posttranslational palmitoylation of two internal lysines (lysines 856 and 963). This modification requires the product of an accessory gene, cyaC, which is located nearby cyaA on *B. pertussis* chromosome.

CyaA has been shown to bind to and invade a variety of cell types including cells lacking membrane traffic like mammalian erythrocytes [Rogel et al., 1992]. This suggested that the catalytic domain of CyaA is directly translocated across the plasma membrane of target cells. The internalization of the catalytic domain into the cell cytosol is calcium and temperature-dependent and depends upon the plasma membrane potential [Rogel et al., 1992] [Karimova et al., 1998] [Otero et al., 1995]. However, the molecular mechanisms by which the toxin transports its N-terminus catalytic domain across the membrane remain largely unknown to date. Furthermore no specific receptor has been reported for CyaA binding.

The physiological consequences of cellular intoxication by CyaA were characterized in vitro in phagocytes. Confer and Eaton first showed that the Cya A extracted from *B. pertussis* increases the intracellular cAMP level in neutrophils or macrophages leading to an inhibition of chemotaxis and bactericidal functions such as superoxide generation and phagocytic abilities [Confer et al., 1982]. These activities were later confirmed with purified toxins or with bacterial mutants genetically deleted of CyaA [Pearson et al., 1987; Friedman et al., 1987] [Njamkepo at al., 2000]. On the contrary, and despite significant changes in their cAMP content, the viability of cell lines from non-hematopoietic origin appeared to be unaffected by the CyaA intoxication [Bassinet et al., 2000]. Moreover, the present inventors previously demonstrated that *B. pertussis* CyaA can trigger macrophage apoptosis in vitro [Khelef et al., 1993; Khelef et al., 1995] and in vivo [Gueirard at al., 1998]. In these models, genetic deletion of CyaA abolished macrophage apoptosis, but not neutrophil death, suggesting that CyaA i) is mainly responsible for macrophage apoptosis, ii) might be responsible for neutrophil apoptosis, but that another factor may also be responsible.

Besides that, in vivo studies performed in a murine model of *B. bronchiseptica* infection (the animal homologue of *B. pertussis* whose CyaA is closely related) demonstrated that the major target of *B. bronchiseptica* CyaA toxicity is a GM-CSF-dependent and cyclophosphamide-sensitive population that controls the early steps of infection [Harvill et al., 1999]. These criterions identified neutrophils and possibly other cells including macrophages or dendritic cells but no data is disclosed or suggested that the CD11b cell receptor is involved in the targeting by Cya A. These populations of target cells for CyaA is the same that limits the early phases of infection and favors the development of an adaptive immune response that controls the latter phases of infection [Harvill et al., 1999].

Unlike other toxins, CyaA has been considered for a long time, as independent of any receptor binding. This is based on the observations that i) CyaA can intoxicate a wide variety of model cell lines from various origin [Ladant et al., 1999] CyaA binds to Jurkat cells and sheep erythrocytes in a non saturable fashion [Gray et al., 1999]. However, some specificity has been found in respect of cells infected by CyaA. Indeed, in vivo studies showed that during murine respiratory infection with *Bordetella* species, CyaA destroyed specifically leukocytes (especially macrophages) without damaging dramatically epithelial cells [Gueirard et al., 1998; Harvill et al., 1999].

It has been proposed in patent application WO 93/21324 to use the recombinant *Bordetella* adenylcyclase to induce a CD4+ T cell or a CD8+ T cell response; however, since no specific receptor for *Bordetella* adenylcyclase was identified, it was not known if the antigen presentation was related to uptake by non professional antigen presenting cell followed by cross-priming and presentation by dendritic cells or if the antigen was targeted to professional Antigen Presenting Cells (pAPC).

In line with their surface phenotype, dendritic cells (high expression of MHCI and II, costimulatory and adhesion molecules) represent the most potent APC in many in vitro assay for the priming of naive T cells [Bell et al., 1999; Viola et al., 1999]. Other APC like resting naive B cells, for example, could even be tolerogenic since injection of resting, male B cells into female hosts leads to the specific tolerization of male-specific CD8+ T cells [Fuchs et al., 1992]. In vitro, naive B cells could delete naive CD8+ T cells via a Fas dependent-mechanism [Bennett et al., 1998].

Moreover, Ag presentation by dendritic cells correlates in vivo with the induction of T cell responses. This has been established for MHCII-restricted Ag presentation. Adjuvant-free Ag injection via the intravenous (iv) route usually does not induce T cell priming [Kyburz et al., 1993; Aichele et al., 1994; Aichele et al., 1995] and leads to Ag presentation by non-specific B cells [Guery et al., 1997] [Zhong at al., 1997; Reis e Sousa et al., 1999] and, eventually dendritic cells [Crowley et al., 1990] [Zhong et al., 1997; Reis e Sousa et al., 1999]. In contrast, local immunization strategies like subcutaneous (sc) immunization in the presence of adjuvant usually, induces T cell priming and targeted Ag presentation by Langerhans cell migrating from the skin to the LN draining the immunization site. In this case, B cells and macrophages are not involved [Guery et al., 1996]. Similar results were obtained after sc or intradermic (id) DNA immunization for MHCII and MHCI-peptide complexes: dendritic cells can be directly transfected at the local site of injection and then migrate to the afferent LN via afferent lymphatics [Condon at al., 1996; Casares et al., 1997; Porgador at al., 1998]. The migration is known as a key event of immunity since mechanical disruption of afferent lymphatics abrogates T cell response to skin sensitizers or skin grafts [Zinkemagel et al., 1997].

Therefore, targeting to dendritic cells is essential for $CD4^+$ and $CD8^+$ T cell stimulation. Since most antibody responses are dependent upon $CD4^+$ T cell help, targeting antigen to dendritic cells is a major goal in vaccination.

Applicants have been interested in studying the presentation of adenylcyclase of *Bordetella* species by T cell, and have identified a specific receptor molecule present on specific cells, that interacts with CyaA and opens new possibilities for the use of CyaA as a proteinaceous vector for molecules of interest.

Genetically detoxified bacterial toxins represent candidates as vaccine vectors, in particular for T epitope, due to their ability to invade eukaryotic cells (Ladant et al., 1999). However, few proteinaceous vectors were shown to prime CTL responses in vivo (Ballard et al., 1996, Cabonette et al., 1999). Moreover, despite numerous in vitro promising studies, no vector was shown to be exclusively targeted to pAPC particularly to dendritic cells and more particularly to myeloid dendritic cells.

The inventors have further shown that other cells, especially neutrophils, could be targeted by the vectors of the present invention.

The invention provides means that may at least in part, fulfil these needs and proposes new vectors that would specifically target molecules to determined populations of pAPC for example, to enable stimulating immune response.

Moreover, molecule targeted to the pAPC and specific leukocytes would enable the manufacturing of new vectors useful to deliver biologically active molecule to the proximal environment of these cells. These molecules, for example, could modulate the functional properties of the targeted cells or those involved in the immune response or in the inflammatory response.

Indeed, the inventors have found that *Bordetella pertussis* adenylcyclase toxin binds specifically with a cellular receptor designated (CD11b/CD18) $\alpha_M/\beta_2$ receptor and that this interaction is required for the intracellular delivery of the adenylcyclase domain to the cytosol of cells and subsequent for cell death. $\alpha_M/\beta_2$ (CD11b/CD18) integrin is a dimer of the $\beta_2$ integrin family, the expression of these integrins being restricted to leukocytes. CD11b/CD18 $\alpha_M/\beta_2$ displays a pattern of expression in mouse and human, which is restricted to neutrophils/granulocytes, macrophages, dendritic cells, NK cells and subsets of B and T CD8+ lymphocytes (Jeyaseelan et al., 2000, Arnaout et al., 1990).

Therefore, this receptor would represent an ideal target for new vectors, designed in particular for T epitope immunization.

Applicants have shown in the present invention that the *Bordetella* adenylcyclase can be used to target a molecule in vivo specifically to CD11b expressing cells.

In particular, Applicants have shown in the present invention that a peptide antigen comprised in the *Bordetella pertussis* adenylcyclase toxin can efficiently be targeted specifically to the surface of dendritic cells, translocated in the cytosol of said dendritic cells and prime a CTL response.

In a specific embodiment, said response is obtained bypassing adjuvant requirement and CD4+ T-cell help.

It has also been shown that genetically modified adenylcylase can be chemically coupled to a peptide of interest to target said peptide to CD11b expressing cells, especially the cytosol of dendritic cells.

This invention thus provides new efficient immunogenic composition as well as new drug delivery vector to CD11b expressing cell

DETAILED DESCRIPTION OF THE INVENTION

This invention relates to the use of *Bordetella* adenylcyclase in the manufacturing of a proteinaceous vector for targeting a molecule of interest specifically to CD11b expressing cells.

The invention also relates to the use of a *Bordetella* adenylcyclase wherein said adenylcyclase is recombined with an antigen and especially modified by insertion of a peptide of interest or modified by insertion of a molecule of interest for the preparation of a composition for the targeting of said peptide or molecule specifically to CD11b expressing cells.

The term "specifically" means within the context of the present invention that the adenylcyclase when used as a vector for a molecule of interest, is preferentially directed to CD11b expressing cells, thereby offering means to target the molecule of interest at the surface of said cells or within said cells in a selective way with respect to other cells.

In one embodiment of the invention, the molecule of interest is essentially directed to CD11b expressing cells.

As used herein, the term "CD11b expressing cells" relates to the cells that express the CD11b/CD18 $\alpha_m\beta_2$ receptor on their surface. In particular, these cells are granulocytes/neutrophils, macrophages, NK cells, subsets of T CD8+ and B cells and myeloid dendritic cells.

Since CD11b expressing cells and more specifically the myeloid dendritic cells, the neutrophils and the macrophages are involved in essential functions of the immune and innate defence system, in particular in inflammatory and specific immune responses, the invention relates to the manufacturing of a proteinaceous vector or a composition capable of targeting a molecule or a peptide of interest to these CD11b expressing cells especially to myeloid dendritic cells, neutrophils or macrophages.

In particular, in one embodiment, the targeting of said molecule or peptide is effective in vivo.

The invention thereby provides means appropriate for the design of compositions suitable for administration to animal or human hosts requiring targeting of certain leukocytes and in particular myeloid dendritic cells, neutrophils or macrophages.

Bordetella adenylcyclase is the calmodulin-dependent adenylcyclase secreted in Bordetella species or fragment thereof, said fragment retaining the function properties of the adenylcyclase, a major virulence factor mandatory for the initial phases of bacterial colonization in the lung. The adenylcyclase is synthesized and secreted in the form of a polypeptide of 1706 amino acids: The calmodulin-dependent catalytic activity is localized in the first 400 amino acids. In order to be active, said adenylcyclase toxin is rendered invasive and hemolytic when post-traductionally modified by the coexpression of the cyaC gene product.

The following specific features of Bordetella adenylcyclase toxin indicate that this toxin can be used in the manufacturing of a proteinaceous vector for targeting in vivo a molecule of interest to CD11b expressing cells:

a) this adenylcyclase binds specifically to CD11b expressing cells b) the N-terminal catalytic domain is translocated into the cytosol of those CD11b expressing cells.

c) the C-terminal domain binds to the membrane of CD11b expressing cells and could internalize by endocytic pathway.

d) epitope chemically coupled to genetically modified adenylcyclase can elicit in vivo specific CTL responses.

The expression "adenylcyclase" encompasses, within the present invention, natural or modified adenylcyclase, including genetically or chemically modified adenylcyclase, providing the resulting product is able to target a molecule of interest specifically to CD11b expressing cells.

The invention thus relates to the use of Bordetella adenylcyclase as defined above and more particularly to the use of a modified or recombinant, adenylcyclase for targeting a molecule of interest specifically to CD11b expressing cells.

More specifically, recombinant adenylclases include adenylcyclases which have been genetically modified to provide either adenyclases with peptide sequence or cysteine residues inserted within the catalytic domain, or truncated adenylcyclases lacking all or part of their catalytic domain.

Due to the specific interaction between Bordetella adenylcyclase toxin and CD11b/CD18 $\alpha_m\beta_2$ receptor, the molecule of interest is specifically targeted at least to the surface of CD11b expressing cells. In a particular embodiment of the invention, the Bordetella adenylcyclase toxin is used in the manufacturing of a proteinaceous vector to deliver the molecule of interest either in the cytosol of CD11b expressing cells, at the surface of CD11b expressing cells or into the endocytic pathway of CD11b expressing cells.

Expression vectors for the preparation of recombinant Bordetella adenylcyclase are described in patent application WO 93/21324 (Institut Pasteur). Novel expression vectors for the preparation of genetically modified Bordetella adenylcyclase appropriate for chemical coupling of a peptide of interest are also described in the experimental part hereafter. More specifically, expression vectors may be constructed directing the expression of both the cyaA gene and the cyaC gene (Sebo et al., 1991). In parallel, a secondary plasmid carrying genes necessary for the secretion of the cytotoxic adenylcyclase in E. coli, such as hlyB and hlyD as described for example in Meckman et al., 1985 can be constructed. In particular, the expression plasmid pCACT3 described in WO 93/21324 can be used. Using this plasmid, the adenyclyclase may be expressed in E. coli and possibly secreted by this bacterium in large amounts. It is also readily purified for example using affinity chromatography on CaM Affi-Gel resin or other published procedures, as those using DEAE-sepharose and phenyl-sepharose (Guermonprez et al., 2000).

In one embodiment of the invention, the adenylcyclase is a recombinant genetically modified adenylcyclase. In particular, mutations such as point mutations, deletions or insertions can be obtained using usual site-directed or random mutagenesis techniques, provided that the domains necessary for binding to CD11b expressing cells and, optionally for translocation in the cytosol are still functional. Assays to evaluate specific binding of recombinant toxins and fragments thereof, to CD11b expressing cells and optionally subsequent translocation of the catalytic domain are described in the following experimental part.

In another embodiment of the invention, the recombinant Bordetella species adenylcyclase is a fragment of the native, modified or recombinant Bordetella species adenylcyclase toxin, wherein said fragment is capable of binding the CD11b receptor. In particular, it has been found in the present invention that fragment encompassing residues 373 to 1706 (CyaA 373-1706) contains the structures essentially required for the interaction with the CD11b/CD18 receptor. Thus, a preferred fragment of the Bordetella species adenylcyclase toxin is the Bordetella adenylcyclase toxin lacking all or part of the N-terminal catalytic domain, and more specifically Bordetella pertussis adenylcyclase lacking all or part of residues 1-373.

Specific binding to CD11b can be assessed in vitro with anti-CD11b monoclonal antibodies as illustrated in the examples.

In order to be used in the manufacturing of proteinaceous vector or the preparation of a composition, the adenylcyclase is preferably non toxic. Non toxic mutants of the adenylcyclase toxin are well described in the Art. (Betsou et al., 1993; Betsou at al., 1995.

In a preferred embodiment of this invention, the adenylcyclase is isolated from Bordetella pertussis.

In specific embodiments, the molecule of interest is selected in the group comprising: peptides, glycopeptides, lipopeptides, polysaccharides, oligosaccharides, nucleic acids, lipids and chemicals.

In specific embodiments, a molecule of interest is a heterologous antigen. As used herein, the term "heterologous" refers to an antigen other than the adenylcyclase which is used in the vector itself.

In a preferred embodiment of the invention, the manufacturing of the proteinaceous vector comprises the step of inserting a heterologous molecule and especially a peptide in the catalytic domain of the adenylcyclase at a permissive site.

As used herein, the term "permissive site" relates to a site where the heterologous molecule and especially a peptide can be inserted without substantially affecting the desired functional properties of the adenylcyclase toxin, i.e. without affecting the domains necessary for the specific binding to CD11b/CD18 receptor and advantageously without affecting the process of translocation of the catalytic domain. In a preferred embodiment, the capacity of the CyaA toxin to promote the synthesis of cAMP in the targeted cells is further maintained.

Methods to select for permissive sites are presented for example in WO93/21324 and in Ladant et al., 1992. In particular, a methodology using a double selection (resistance to an antibiotic and calorimetric test on dishes by α-complementation) enables to identify readily oligonucleotides insertions (which preserve the reading frame) in the portion of the gene coding for the N-terminal catalytic domain of the toxin. The functional consequences of these mutations on the catalytic activity of the toxin may be readily analysed, both genetically (functional complementation of an *E. coli* cya⁻ strain) and biochemically (characterization of the stability of the modified adenylcyclases, of their enzymatic activity, of their interaction with caM, etc.). This methodology has enabled a large number of mutations to be screened in order to identify the sites which are potentially advantageous for the insertion of antigenic determinants.

In specific embodiments of the invention, a permissive site is selected from the group consisting of residues 137-138, residues 224-225, residues 228-229, residues 235-236 residues 317-318 and residues 335-336 of theBordetella pertussis adenylcyclase.

However, other permissive sites may be used in the present invention, that can be identified for example by use of the methodology indicated above, especially sites between residues 400 and 1700.

The manufacturing of the proteinaceous vector can also comprise a step of fusing a molecule of interest, for example a heterologous peptide, at the N-terminal extremity of a *Bordetella* adenylcyclase lacking all or part of its N-terminal catalytic domain, and more preferably, *Bordetella pertussis* adenylcyclase lacking residues 1-373.

In a preferred embodiment of the invention, the adenylcyclase according to one of the above definitions is used in the manufacturing of a proteinaceous vector or in the preparation of a composition specifically designed to prime CD8+ cytoxic T-cell response (CTL response) said response follows the targeting of the adenylcyclase modified (especially recombined or conjugated) with a molecule of interest to CD11b expressing cells, followed by the translocation of the molecule of interest to the cytosol of said CD11b expressing cells, and in particular to myeloid dendritic cells. In this context, the molecule of interest is or comprises preferably an epitope or an antigen.

As used herein, the term "epitope" refers to a heterologous molecule and especially a heterologous peptide that can induce an immune response.

In specific embodiments, the antigen is selected from the group consisting of an intracellular bacterial cell antigen, a tumoral cell antigen, a viral antigen, a fungus antigen or a parasite cell antigen.

In a preferred embodiment of the invention, the adenylcyclase, i.e., a natural, modified or recombinant adenylcyclase according to one of the above definitions is used in the manufacturing of the proteinaceous vector or in the preparation of a composition specifically designed to prime CD4+ cells response said response follows the targeting of the adenylcyclase modified (especially recombined or conjugated) with a molecule of interest to CD11b expressing cells, in particular myeloid dendritic cells. In this context, the molecule of interest is or comprises preferably an epitope or an antigen.

A molecule of interest can be especially an antigen selected from the group consisting of: a poliovirus antigen, an HIV virus antigen, an influenza virus antigen, a choriomeningitis virus epitope, a tumor antigen.

The functional properties of the CD11b expressing cells define furthermore a novel use of the *Bordetella* adenylcyclase toxin in the manufacturing of a proteinaceous vector for drug targeting to these specific cells. In this context, in one specific embodiment of the invention, the so-called molecule of interest is a drug. Said drug may be chemically or genetically coupled to the adenylcyclase. Method for coupling a drug to a polypeptide are well known in the Art and comprise for example disulfide linkage by using N-pyridyl sulfonyl-activated sulfhydryl.

Advantageously, a molecule of interest is an anti-inflammatory drug which is, when coupled to the adenylcyclase toxin, specifically targeted to the surface of the cells involved of the inflammatory response, such as neutrophils.

In particular, it is shown for the first time in the Experimental part that it is possible to graft molecules to CyaA by a chemical linkage or by genetic insertion for in vivo targeting to CD11b+ antigen presenting cells and particularly to the cytosol of CD11B+ antigen presenting cells. Indeed, when coupling a molecule corresponding to a given CD8+ T-cell epitope to the catalytic domain of detoxified CyaA, either by means of a disulfide bond or by genetic insertion, it has been found that the engineered molecule can elicit in vivo specific CTL response, thereby showing that said CD8+ T-cell epitope is translocated into the cytosol of CD11b-expressing cells.

More specifically, antigen presentation for selective CD8+ cytotoxic cells priming is mainly performed by myeloid dendritic cells.

Accordingly, in a specific embodiment, the recombinant adenylcyclase used for the manufacturing of proteinaceous vector is a genetically modified adenylcyclase containing one or more molecule(s) chemically coupled by means of a disulfide bond to genetically inserted cysteine residue(s) located within the catalytic domain of said adenylcyclase.

Indeed, multiple molecules can be chemically coupled to the adenylcyclase by means of a disulfide bond to different cysteine residues located at different permissive sites within the catalytic domain.

Applicant has also shown that CTL specific for the vectorized antigen can be primed in vivo after a single intravenous injection of the recombinant toxin, especially with no need to provide an heterologous adjuvant. These results shown in the experimental part and in particular the specific targeting of the epitope to myeloid dendritic cells enable new immunization strategies that bypass the requirement for adjuvant and CD4+ T cell help.

Therefore, the invention also relates to the use of a *Bordetella* adenylcyclase toxin recombined with a molecule and especially a peptide of interest for the preparation of a composition formulated for intravenous administration and enabling a CD8+ T cell immune response in vivo, said composition being free of a heterologous adjuvant. The invention also concerns this composition as such.

The invention in particular also relates to a new immunogenic composition formulated for administration, especially intravenous administration, in an animal or human host, characterized in that it comprises a recombinant *Bordetella* adenylcyclase which comprises an antigen inserted in the catalytic domain.

The invention further relates to a pharmaceutical composition for administration in a human or an animal formulated for targeting a molecule of interest specifically to CD11b expressing cells characterized in that said molecule of interest is coupled to a *Bordetella* species adenylcyclase.

In one preferred embodiment, the molecule of interest is selected in the group comprising: peptides, glycopeptides, lipopeptides, polysaccharides, oligosaccharides, nucleic acids, lipids and chemicals.

In another preferred embodiment, the molecule of interest is an antigen.

In another specific embodiment, the pharmaceutical or immunogenic composition comprises a nucleic acid construction encoding the recombinant *Bordetella* species adenylcyclase comprising a recombinant *Bordetella* species adenylcyclase coupled to a molecule of interest.

In specific embodiments, the adenylcyclase is from *Bordetella pertussis* toxin.

In other specific embodiments, the adenylcyclase toxin is a genetically modified toxin. In one preferred embodiment, the adenylcyclase is a non toxic adenylcyclase, especially a detoxified adenylcyclase.

In one preferred embodiment, the genetically modified adenylcyclase is able to translocate the molecule of interest specifically in the cytosol of CD11b expressing cells.

In particular, said genetically modified adenylcyclase is a *Bordetella* adenylcyclase lacking all or part of its catalytic N-terminal domain, and more specifically *Bordetella pertussis* adenylcyclase lacking residues 1-373.

Advantageously, the genetically modified adenylcyclase comprises one or more cysteine residues inserted within the catalytic domain at permissive sites. Such genetically modified adenylcyclase can be coupled to one or more molecule(s) of interest by means of disulfide bond(s) at the inserted cysteine residue(s).

In a preferred embodiment, the molecule, and especially an antigen is inserted in the permissive sites selected from the group consisting of residues 137-138, residues 224-225, residues 228-229, residues 235-236 and residues 317-318, and residues 335-336 of the *Bordetella pertussis* adenylcyclase, or the molecule is fused to the N-terminal part of a *Bordetella* adenylcyclase lacking all or part of its N-terminal catalytic domain, and more specifically to the N-terminal part of a *Bordetella pertussis* adenylcyclase lacking residues 1-373.

In a specific embodiment, the molecule is an antigen which is an intracellular bacterial cell antigen, a tumoral cell antigen, a viral antigen, a fungus antigen or a parasite cell antigen.

In preferred embodiments, a molecule of interest is an antigen selected from the group consisting of: a poliovirus epitope, an HIV virus, an influenza virus antigen, a choriomeningitis virus antigen, a tumor antigen.

In another embodiment, the genetically modified toxin is able to deliver the molecule of interest specifically at the surface of CD11b expressing cells or into the endocytic pathway.

The applicants have shown that in vivo intravenous administration of the immunogenic composition in an animal or human host as defined in the present invention without adjuvant(s) is sufficient to promote efficiently an immune response in said animal or human host.

In particular, the immunogenic compositions of the invention are capable of inducing or stimulating, in vivo or in vitro an immune cell response involving specifically dendritic cells.

As a consequence, in a specific embodiment, the immunogenic or pharmaceutical composition is advantageously devoid of priming adjuvants commonly used in the Art, such as aluminium hydroxide.

In one specific embodiment, the molecule of interest is a drug, preferably an anti-inflammatory drug.

Furthermore, the invention also relates to the use of the immunogenic composition as defined above for the preparation of a vaccine or an immunotherapeutic composition, for administration to an animal or human host.

As used herein, the term "immunotherapeutic composition" relates to a composition which leads to an immunological response and which is associated to therapeutic treatments, such as treatment against cancers, viral infections, parasites infections or bacterial infections.

The invention further relates to a method to immunize an animal or human host, wherein said method comprises the steps of:

a) providing an immunogenic composition as defined above;

b) administering said immunogenic composition, preferably via intravenous route, to said host in order to promote an immune response.

The invention finally relates to a proteinaceous vector for delivery of a molecule of interest, specifically to CD11b expressing cells, characterized in that said vector comprises a *Bordetella* species adenylclyclase and more preferably a recombinant or modified *Bordetella* species adenylcyclase coupled to said molecule of interest.

The proteinaceous vector is able to target a molecule of interest to CD11b expressing cells via the specific binding of *Bordetella* adenylcyclase with CD11b/CD18 $\alpha_m\beta_2$ which is present on the surface of specific cells. In one specific embodiment, the vector is also able to deliver the molecule of interest specifically in the cytosol of CD11b expressing cells.

In specific embodiments, the proteinaceous vector is able to target a molecule of interest to dendritic cells, particularly myeloid dendritic cells, or to neutrophils.

The molecule of interest is chemically or genetically coupled to the adenylclase, more preferably the recombinant adenylcyclase toxin. Method for coupling a molecule to a polypeptide are well known in the Art. As an example, the inventors showed that a biotin derivative, biotin HDPD can be selectively coupled on an unique cysteine residue genetically inserted within the catalytic domain. Synthetic peptides have been coupled similarly to the cysteine containing adenylcyclase toxin, or to genetically modified adenylcyclase devoid of native cysteine residue but containing an unique genetically inserted cysteine residue.

In another specific embodiment, a molecule of interest coupled to the adenylcyclase is an epitope chemically coupled to a genetically modified adenylcyclase devoid of native cysteine residue but containing genetically inserted cysteine residue(s) at a permissive site within its catalytic domain.

In a specific embodiment, the proteinaceous vector comprises a genetically modified adenylcyclase. In one preferred embodiment, the adenylcyclase is a recombinant non toxic adenylcyclase from *Bordetella pertussis*.

The invention more specifically relates to a proteinaceous vector which consists of a recombinant *Bordetella* adenylcyclase lacking all or part of the N-terminal catalytic domain, and more preferably a *Bordetella pertussis* lacking residues 1-373.

Another preferred proteinaceous vector of the invention is a genetically modified *Bordetella* adenylcyclase devoid of native cysteine residue, but containing genetically inserted cysteine residue(s) at a permissive site within the catalytic domain.

Advantageously, in one specific embodiment of the invention, a drug to be delivered is an anti-inflammatory drug which is, when coupled to the adenylcyclase toxin, targeted to the surface or to the cytosol of the cells involved of the inflammatory response, such as neutrophils.

The following examples will illustrate the present invention without limiting the scope of the claimed invention. More specifically, in part A, experimental data are shown that reveal the specific binding of adenylcyclase toxin to CD11b/CD18 receptor, and in particular the specific binding of adenycyclase toxin to CD11b expressing cells in vitro. In part B, the experimental results show the possibility to target a genetically coupled molecule, more particularly an antigen in vitro and in vivo specifically to the cytosol of CD11b expressing cells, and in particular to myeloid dendritic cells. Moreover, the results show that the targeting is mediated by the CD11b receptor and that CTL priming is observed after systemic immunization in the absence of adjuvant. In part C., it is shown that specific coupling of epitope peptides by means of a disulfide bond on CyaA fragments can be carried out to provide new proteinaceous vectors. In part D., it is shown that, only the C-terminal part of CyaA is necessary and sufficient for interaction with CD11b receptors.

Finally, the results indicate that, unlike many other CTL responses as those raised against cross-priming antigen, CD4+ T cell help was not mandatory for priming of CTL responses.

LEGENDS TO FIGURES

FIGS. 1A to 1E: Saturable binding of CyaA correlates with CD11b expression

A: CyaA binding at the surface of macrophages (J774A.1), B cells (LB27.4), and T cells (EL4) was performed at 37° C. for 20 minutes. Surface-bound CyaA was detected with a biotinylated anti-CyaA polyclonal antibody, revealed by streptavidin-PE and detected by flow cytometry on living cells, as described in the material and methods section. Binding is expressed as ΔMFI=(mean fluorescence intensity value of cells incubated with CyaA)−(mean fluorescence intensity of cells without CyaA).

B, C, D, E: Surface expression of $\beta_2$ integrins on J774A.1, LB27.4 and EL4 cells. CD11a (B), CD11b (C), CD11c (D), and CD18 (E) expression were determined by flow cytometry using specific mAbs coupled to PE. Integrin expression is expressed as ΔMFI=(mean fluorescence intensity value of cells stained with specific mAb)−(mean fluorescence intensity of cells stained with an isotype control mAb).

FIGS. 2A to 2D: CyaA binding to murine cell lines is blocked by anti-CD11b mAb.

Cells were preincubated at 4° C. for 15 minutes with or without 20 μg/ml of specific mAbs and then incubated at 4° C. for 20 minutes with 5 μg/ml CyaA and with 10 μg/ml of specific mAbs if present during the preincubation. Surface-bound CyaA was detected with a biotinylated anti-CyaA polyclonal, revealed by streptavidin-PE and detected by flow cytometry on living cells, as described in the material and methods section.

A, B: Effect of the M1/70 anti-CD11b mAb on the binding of various doses of CyaA. FSDC dendritic cells (a) or J774A.1 macrophages (b) were preincubated with medium alone (○) or with M1/70 anti-CD11b mAb (●) and then incubated with CyaA with or without M1/70 anti-CD11b mAb. Bmax was determined by fitting experimental points obtained from experiments performed without mAbs to ΔMFI=Bmax*[CyaA]/($K_d$+[CyaA]). Binding of CyaA is plot as a % of Bmax plot against CyaA concentration.

C, D: Effect of specific mAbs on a fixed dose of CyaA binding. FSDC (c) or J774A.1 (d) cells were preincubated with or without specific mAbs (anti-CD11a, 2D7, antiCD11b, M1/70 and 5C6, anti-CD11c, HL3, anti-CD18, C17/16, control A95-1) and incubated with CyaA at the fixed concentration of 5 μg/ml. Values of ΔMFI obtained for CyaA binding on cells treated with specific mAbs were normalized as ΔMFI values obtained for CyaA binding without mAb.

FIGS. 3A to 3D: CyaA binding to the human neutrophils is blocked by anti-CD11b and anti-CD18 mAbs.

A, B, C: Fluorescence histograms of freshly purified neutrophils were preincubated with medium alone (A), the 44 anti-CD11b mAb (B) or an isotype-matched control mouse mAb (C) and then incubated with (gray) or without (blank) biotinylated CyaA and revealed by streptavidine-PE. Cell number is plotted against log of PE fluorescence.

D: Effect of specific mAbs on CyaA binding to neutrophils (anti-CD11b, 44, M1/70, anti-CD18, TS/18, control mouse IgG2a, control rat IgG2b, A95-1). Freshly purified neutrophils were preincubated with or without specific mAbs and incubated with CyaA. Values of ΔMFI obtained for CyaA binding on cells treated with specific mAbs were normalized as a % of the ΔMFI values obtained for CyaA binding without mAb.

Figure 4B:
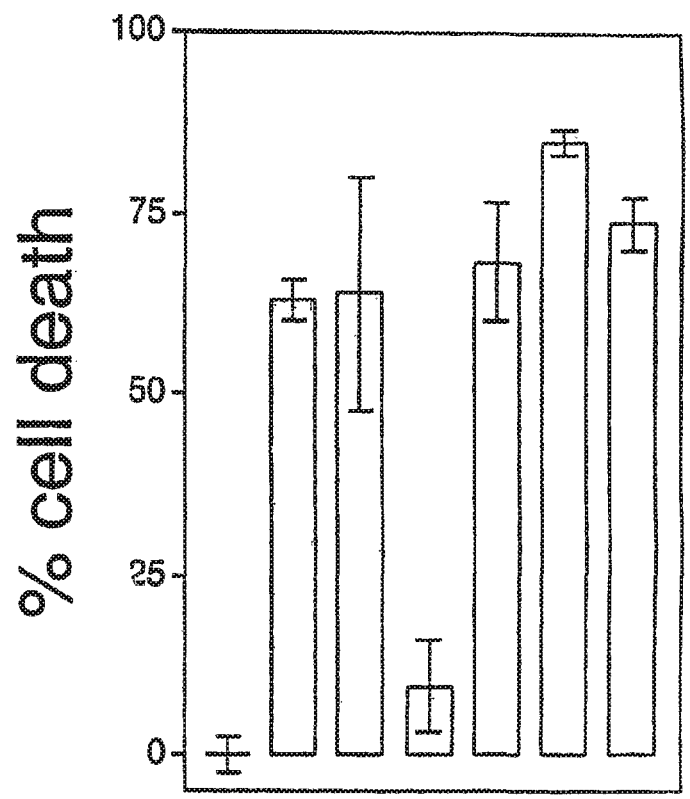

FIGS. 4A and 4B: Intracellular cAMP increase and cell death mediated by CyaA are specifically blocked by an anti-CD11b mAb in J774A.1 cells.

A: Effect of specific mAbs on intracellular cAMP accumulation. J774A.1 cells were preincubated at 4° C. for 1 h with or without 10 μg/ml of specific mAbs (anti-CD11b, M1/70, anti-CD18, C17/16) and then incubated at 37° C. for 20 min with 5 μg/ml CyaA and with 10 μg/ml mAbs if present during the preincubation. Intracellular cAMP contents were determined as described in the materials and methods section.

B: Effect of specific mAbs on CyaA mediated cell death. J774A.1 cells were preincubated at 4° C. for 1 h with medium alone or with 10 μg/ml of specific mAbs (anti-CD11a, 2D7 anti-CD11b, M1170, anti-CD11c, HL3, anti-CD18, C71/16, control, 2.4G2). Then they were incubated at 37° C. for 2 h with 0.5 μg/ml CyaA and with 10 μg/ml of specific mAbs when present during the preincubation. Cell lysis was determined by LDH release using the Cytotox 96™ assay.

FIGS. 5A to 5D: CHO cells bind CyaA and become sensitive to CyaA when transfected with CD11b, but not with CD11c A, B: CyaA binding at the surface of CHO transfectants. CHO cells transfected with human CD11b/CD18 (●), human CD11c/CD18 (○) or mock-transfected (◗) were incubated with various doses of CyaA for 20 min at 37° C. (a) or 4° C. (b). Surface-bound CyaA was detected with a biotinylated anti-CyaA polyclonal antibody, revealed by streptavidin-PE and detected by flow cytometry on living cells, as described in the material and methods section. Binding is expressed as ΔMFI=(mean fluorescence intensity value of cells incubated with CyaA)−(mean fluorescence intensity of cells without CyaA).

C: Intracellular cAMP accumulation in CHO transfectants. CHO cells transfected with human CD11b/CD18 (●), human CD11c/CD18 (○) or mock-transfected (◗) were incubated with or without CyaA for 20 min at 37° C. Intracellular cAMP contents were determined as described in the materials and methods section.

D: Cell lysis in CHO transfectants. CHO cells transfected with human CD11b/CD18, human CD11c/CD18 or mock-transfected were incubated with 5 μg/ml CyaA for 4 h at 37° C. Cell lysis was determined by LDH release using the Cytotox 96™ assay.

FIGS. 6A to 6D: Intravenous immunization with CyaAOVA primes anti-OVA CTL responses in a B cell, CD4 and CD40-independent way.

C57BL/6 WT+/+ (A), CD4−/− (B), CD40−/− (C) or IgM−/− (D) mice were intravenously immunized with 50 μg of CyaAOVA, a genetically detoxified form of CyaA carrying the H-2K$^b$ restricted SIINFEKL epitope from OVA (●, ○) or with CyaAE5, a control detoxified toxin without the OVA epitope (▲, △). Seven days after, animals were sacrificed and splenocytes were restimulated in vitro for 5 days with 10 μg/ml of the pOVA synthetic peptide in the presence of irradiated C57BL/6 splenocytes. CTL activity was assessed in a 4 hours chromium$^{51}$ release assay against H-2K$^{b+}$ EL4 cells previously pulsed (●, ▲) or not (○, △) with pOVA at 10 μg/ml.

FIGS. 7A to 7H: Identification of splenic antigen presenting cells involved in CyaAOVA presentation in vitro or in situ, after intravenous immunization.

The low density fraction of splenocytes presents CyaAOVA to a specific anti-OVA CD8+ T cell hybridoma (A, E):

In vitro assay (A): Low (LDF, ●) and high density (HDF, ▲) fractions or unfractionated total splenocytes from naive mice (TSC, ■, □) were cultured with B3Z, a CD8$^+$ T cell hybridoma specific for the pOVA peptide in the context of H-2K$^b$. After 18 hours of coculture in the presence of the recombinant detoxified CyaA carrying the OVA peptide (CyaAOVA, ●, ▲, ■) or a control peptide (CyaALCMV, □) at various concentrations, IL-2 released in supernatants was measured in a CTLL proliferation assay. Results are expressed in Δcpm and plotted against CyaA concentration during the assay Δcpm=[cpm+CyaA]−[cpm−CyaA]).

Ex vivo assay (E): Spleen cells were obtained from mice previously immunized iv (6-12 hours) with 50 μg of CyaAOVA (●, ▲, ■) or CyaALCMV (○) and fractionated in LDF and HDF. Various numbers of cells recovered from TSC (U), LDF (●, ○) or HDF (A) or unfractionated splenocytes (■) were directly put in culture with B3Z without addition of recombinant CyaA. IL-2 release was assessed after 18 hours of culture as described before. Results, expressed in cpm, are plotted against the number of APC present in each well.

Dendritic Cells (CD11c$^+$) are More Efficient APC for CyaAOVA than the CD11b$^{high+}$ CD11c$^-$ Cells or B Cells (CD45R$^+$) (B, F):

In vitro assay (B): CD11c$^+$ (●) sorted cells from LDF, CD11b$^{high+}$CD11c$^-$ (0) and CD45R$^+$ (■) sorted cells from TSC, were put in culture with B3Z for 18 hours in the presence of various concentrations of CyaAOVA. IL-2 was assessed as above.

Ex vivo assay (F): Cells sorted by flow cytometry from C57BL/6 mice previously (6-12 hours) immunized with 50 μg of CyaAOVA were used as APC. CD11c+ (●), CD11b$^{high+}$CD11c$^-$ (○), CD45R$^+$ (■) sorted cells from low density splenocytes were directly put in culture for 18 hours with B3Z at various numbers of cells per well, without addition of CyaAOVA. IL-2 was assessed as above.

The CD8α$^-$ Myeloid Dendritic Cell Subset is a More Efficient APC for CyaA than the CD8α$^+$ Lymphoid Dendritic Cell Subset (C, G):

CD11c+ low density cells from naive mice (C) or mice previously (6-12 hours) immunized iv with 50 μg CyaAOVA (G) were fractionated in myeloid dendritic cells (CD11c$^+$ CD8α$^-$, ●) and lymphoid dendritic cells (CD11c$^+$CD8α$^+$, ○) by flow cytometry and used as APC in in vitro (C) and ex vivo (G) assays for B3Z stimulation. IL-2 was assessed as above.

B Cell Genetic Depletion does not Impair CyaAOVA Presentation by Splenocytes (D, H):

TSC (■, □), LDF (●, ○) or HDF (▲, △) from C57BL/6 WT mice (■, ●, ▲) or B cell deficient (□, ○, △) were used as APC in an in vitro assay (D, ■, □) or an ex vivo assay (H, ■, ●, ▲, □, ○, △) for B3Z stimulation as in a. Mice were either from naive (D) or previously (1.5 hours) immunized iv with 50 μg CyaAOVA (H). IL-2 was assessed as above.

Figure 8A:
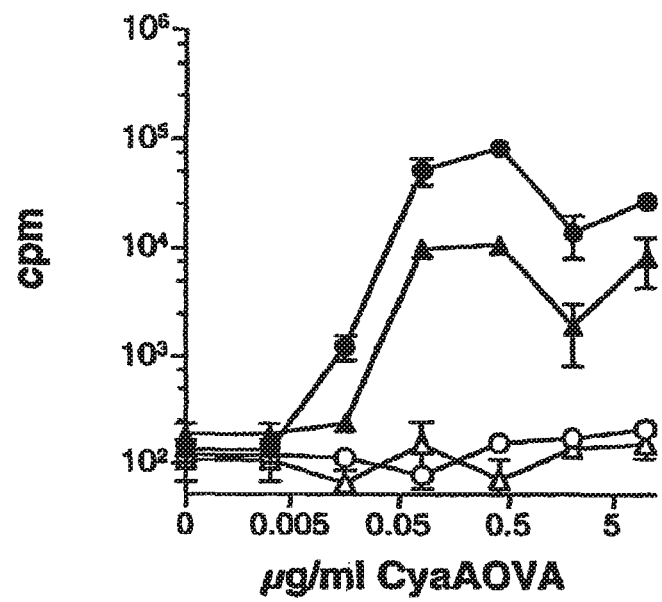
Figure 8B:
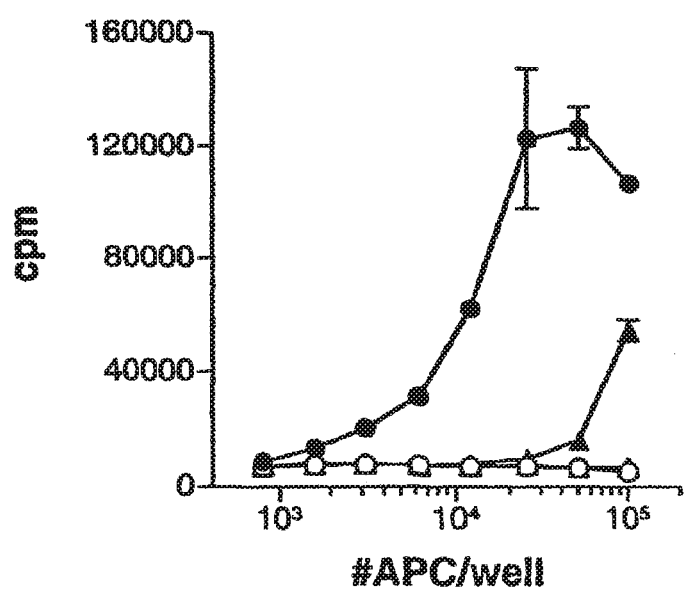
Figure 9F:
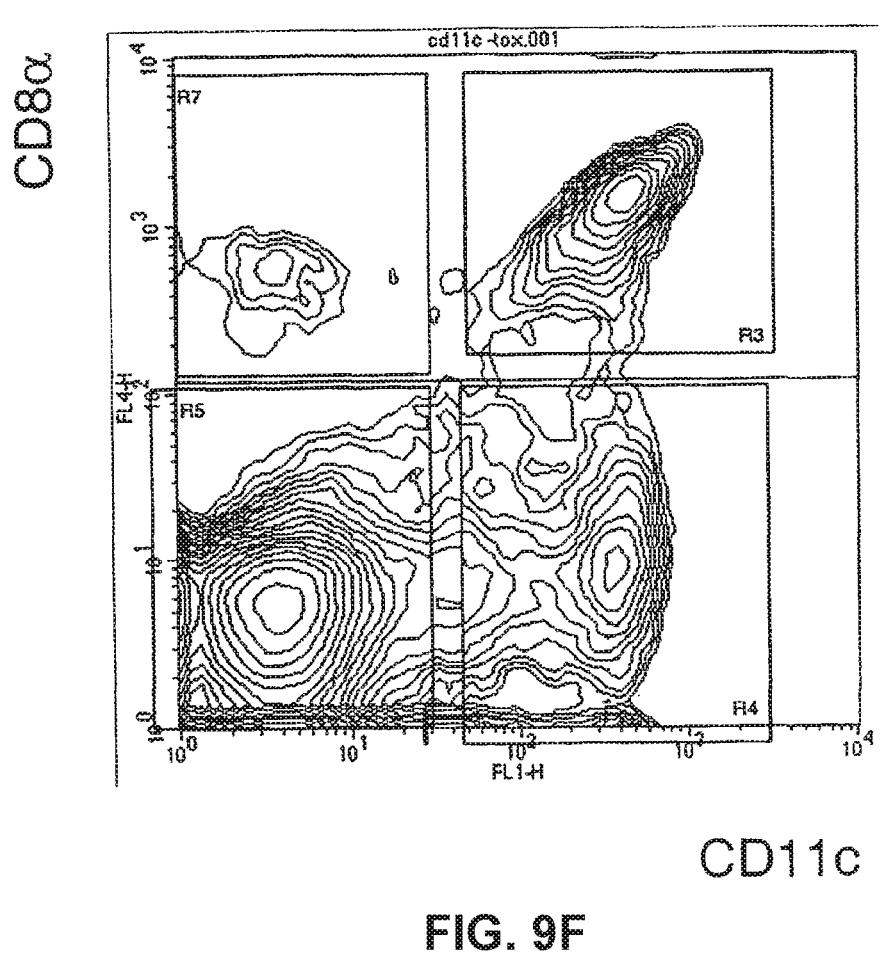
Figure 9G:
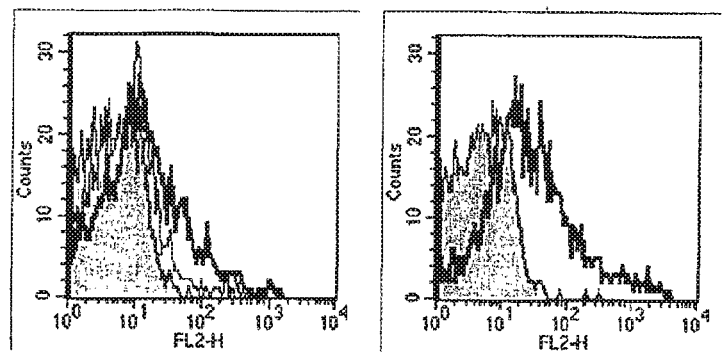
Figure 9H:
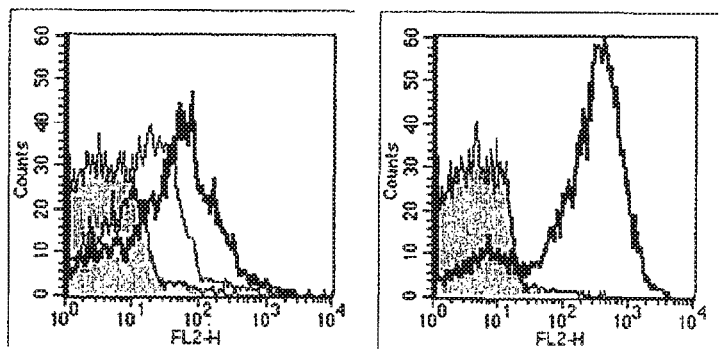
Figure 9I:
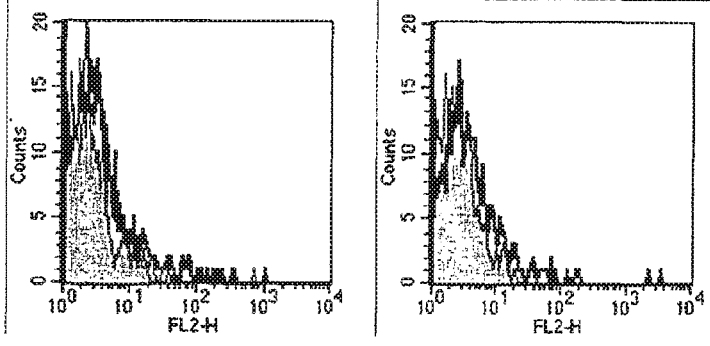
Figure 9J:
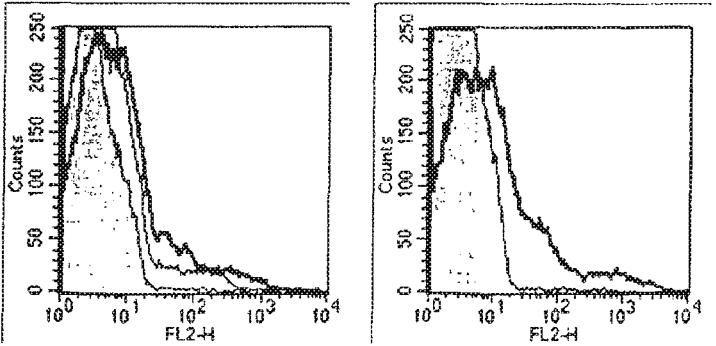

FIGS. 8A and 8B: The presentation of CyaAOVA by dendritic cells requires the TAP transporters in vitro and in vivo after intravenous immunization.

In vitro assay (A): TSC (▲, △) or CD11e (●, ○) sorted cells from control C57BL6 TAP+/+ (▲, ●) or TAP−/− mice (△, ○) were cultured with B3Z in the presence or not of various doses of CyaAOVA. IL-2 was assessed as described in FIG. 6a. Results are expressed in cpm plotted against antigen concentration.

Ex vivo assay (B): TSC (▲, △) or CD11c$^+$ (●, ○) sorted cells from control C57BL6 TAP+/+ (▲, ●) or TAP−/− mice (△, ○) previously iv immunized with 50 μg of CyaAOVA were cultured with B3Z for 18 hours. IL-2 was assessed as described in FIG. 6a. Results are expressed in cpm plotted against the number of cocultured cells.

FIGS. 9A to 9J: Role of $\alpha_m\beta_2$ integrin (CD11b) in CyaAOVA binding to cells.

Binding of CyaAOVA-biotine to TSC is blocked by anti-CD11b (A-E): TSC suspensions were incubated at 4° C. with 10 μg/ml of the anti-CD11b M1/70 mAb or an isotype control mAb or nothing. Then, CyaAOVA-biotine at 2 μg/ml (left panels) or various concentrations (right panel) was added to the cells for 30 nm at 4° C. After a wash, CyaAOVA-biotine was revealed with streptavidine-PE for 30 nm (Strep-PE). Then, after washing, cells were resuspended in PBS containing propidium iodide. The size (FSC) of living cells gated by propidium iodide exclusion was plotted against the Strep-PE fluorescence. The percentage of leukocytes positive for CyaAOVA-biotine was plotted against CyaAOVA-biotine concentration during the staining.

Binding of CyaAOVA-biotine to low density cells correlates with the expression of CD11b (F-J) LDF were triple stained for CD11c, CD8α and CyaOVAbiotine (or medium) or, in separate experiments with CD11c, CD8α, and CD11b (or a control mAb). After a wash, cells were stained for 30 nm with Strep-PE to reveal CyaAOVA-biotine, anti-CD11c-FITC and anti-CD8α-APC. Gates were done on lymphoid DC (CD11c$^+$CD8α$^+$), myeloid DC (CD11c$^+$CD8α$^-$), CD8+ T cells (CD11c$^-$CD8α$^+$) and other cells (CD11c$^+$CD8α$^-$). For each gate, CyaAOVA-biotine staining or CD11b staining is plotted against cell number in separate histograms. Left histograms: LDF suspensions were incubated with 0 (histograms filled in grey), 2.5 (narrow, open histograms) or 10 μg/ml (thick, open histograms) of CyaAOVA-biotine for 30 minutes at room temperature. Right histograms: isotype control-PE (histogram filled in grey), CD11b-PE (thin, open histograms).

FIGS. 10A to 10D: Role of $\alpha_M\beta_2$ integrin (CD11b) in CyaAOVA Presentation by MHC I In vitro antigen presenting assay with TSC (A, B): The same experiments than in a, b were performed with TSC from naive C57BL/6 mice as APC. The stimulation of B3Z was assessed by IL-2 release in coculture supernatants measured in a CTLL proliferation assay. Results are plotted in cpm against CyaAOVA or pOVA concentration.

Ex vivo antigen presenting assay with TSC or CD11b$^+$ and CD11b$^-$ fractions: C57BL/6 mice were intravenously immunized with 50 μg of CyaAOVA (c) or 10 μg of pOVA (d). CD11b$^+$ (●) and CD11b$^-$ (○) cells were sorted by flow cytometry from TSC (△) and put in culture at various cell number per well with B3Z. After 18 hours of coculture, the stimulation of B3Z was assessed by IL-2 release. Results, expressed in cpm, are plotted against the numbers of APC from immunized animals present in each well.

FIG. 11: Summary of the methodology for chemical coupling of epitopes to recombinant CyaA through disulfide bond.

Figure 12:
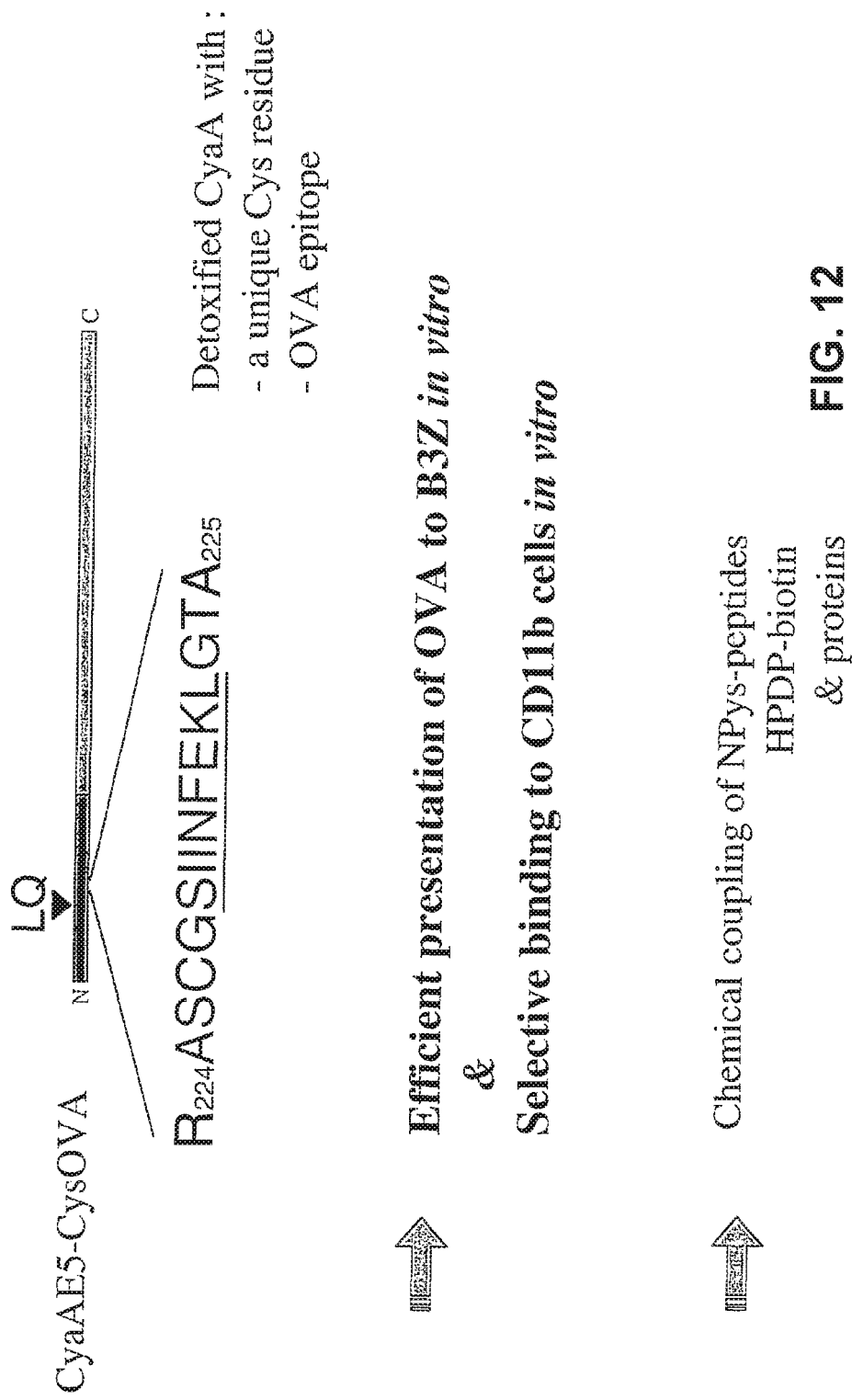

FIG. 12: A diagram of a vector for chemical coupling of CTL epitopes

Figure 13:
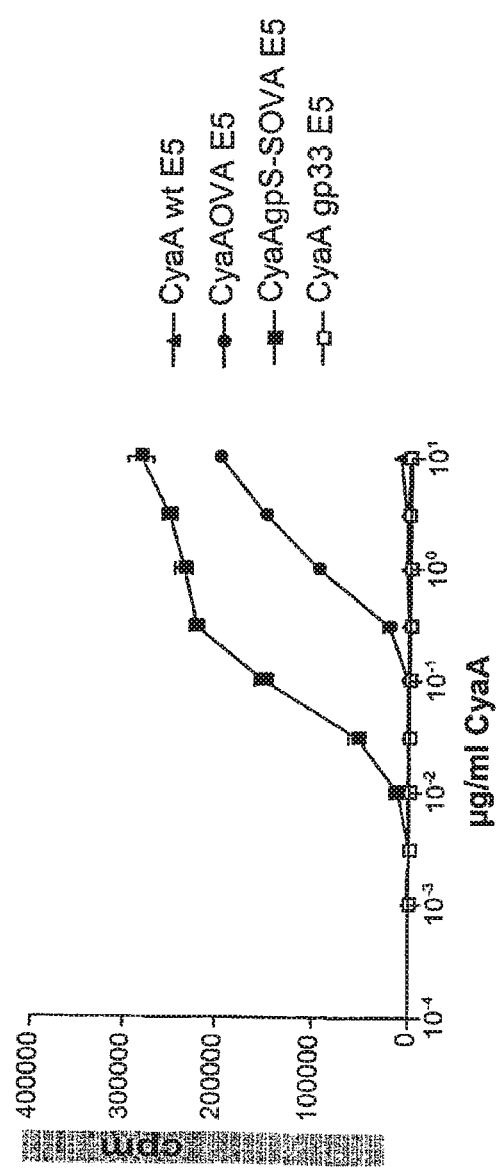

FIG. 13: A graph showing IL-2 release by B3Z measured in a CTLL proliferation assay.

$3 \cdot 10^5$ spleen cells from C57Bl/6 mice were cocultured for 18 h with 105B3Z cells in the presence of various concentrations of cyclases. The IL2 release by B3Z was measured in a CTLL proliferation assay.

Figure 14A:
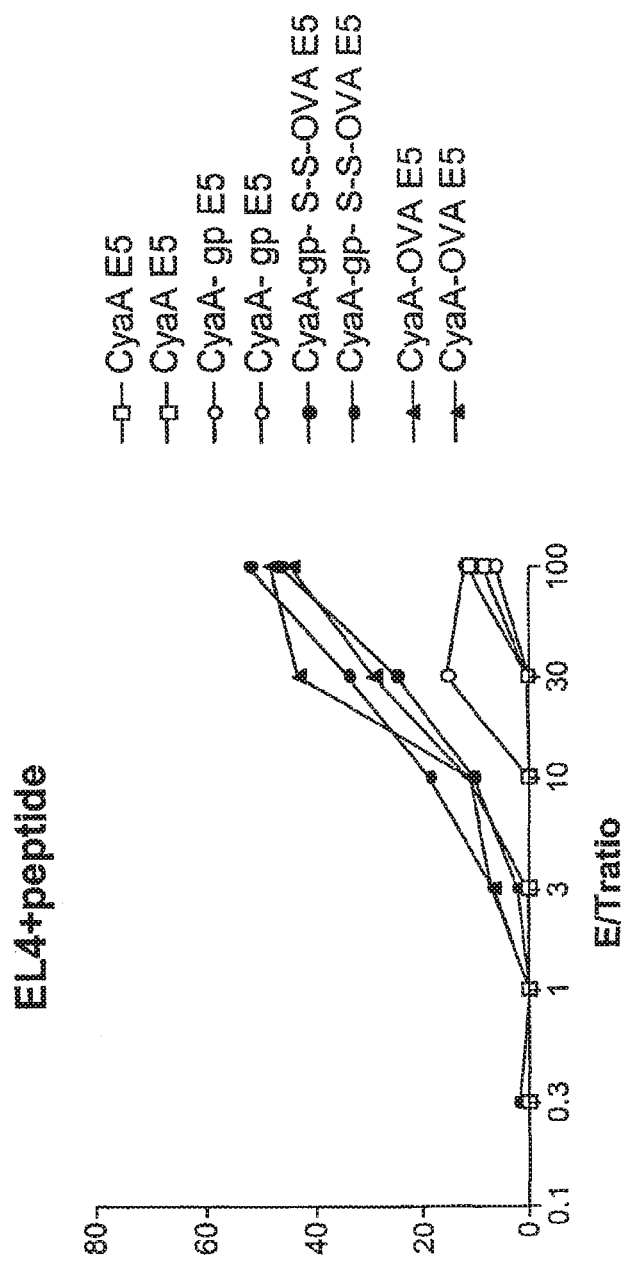
Figure 14B:
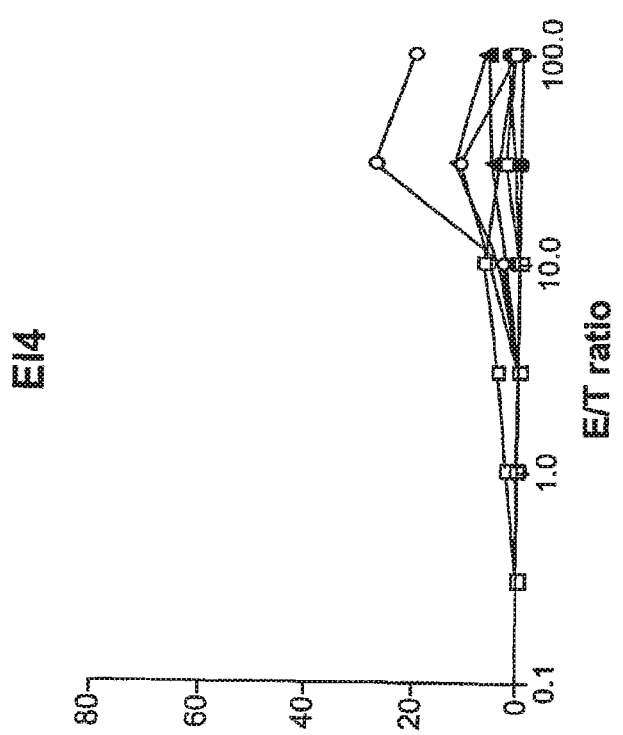

FIGS. 14A and 14B: A graph showing cytotoxic activity measured on $^{51}$Cr-labelled EL4 target cells pulsed (A) or not (B) with 50 µM of the OVA peptide.

C57BL/6 mice were iv injected with 50 µg of the various CyaA. Seven days later, spleen cells were in vitro stimulated with OVA peptide. The cytotoxic activity was measured on 51 Cr-labelled target cells.

FIGS. 14A and 14B show the in vivo capacity of the proteinaceous vectors of the invention to induce OVA-specific CTL responses.

Figure 15A:
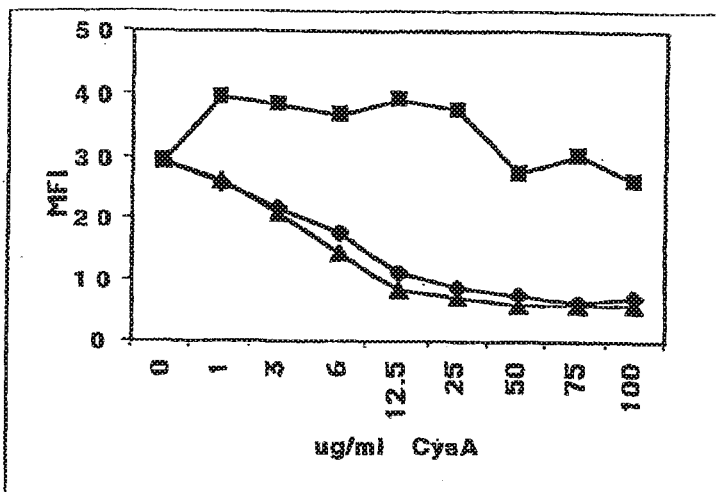
Figure 15B:
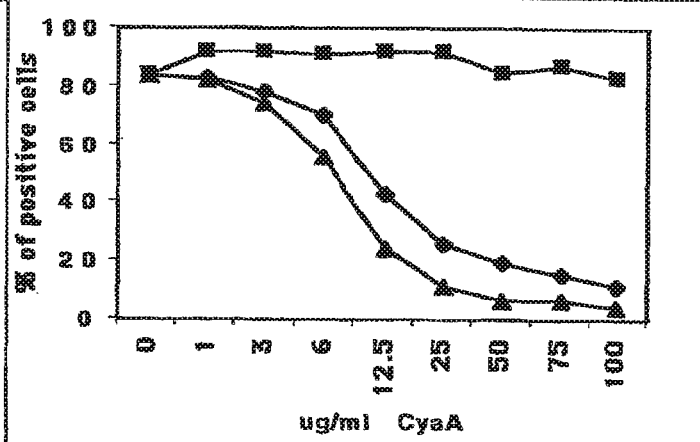
Figure 15C:
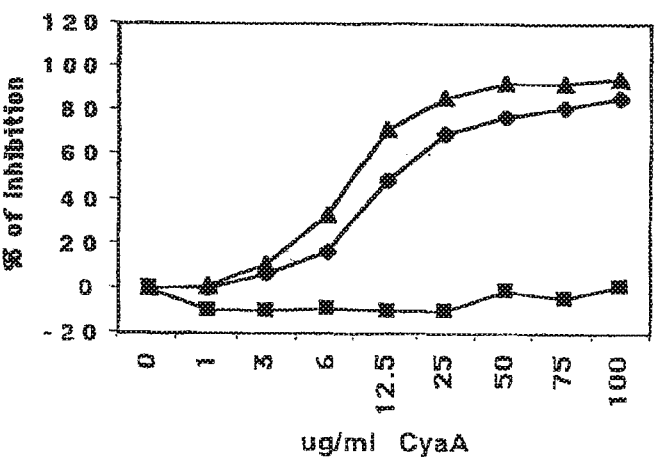

FIGS. 15A to 15C: Inhibition of CyaA Binding to CD11b by CyaA-E5 and CyaA Fragments CHO cells transfected with CD11b/CD18 were preincubated on ice for 1 hour with different concentrations of CyaA-E5 (black triangle), CyaA 1-383 (black square) or CyaA-373-1706 (Black diamond) and then incubated on ice for 30 min with 5 µg/ml of biotinylated CyaA-E5. Surface bound cyclase was revealed using streptavidin-PE and analyzed by flow cytometry on living cells. Results are expressed as mean fluorescence intensity (A), percentage of positive cells (B) and percentage of inhibition (C).

Figure 16:
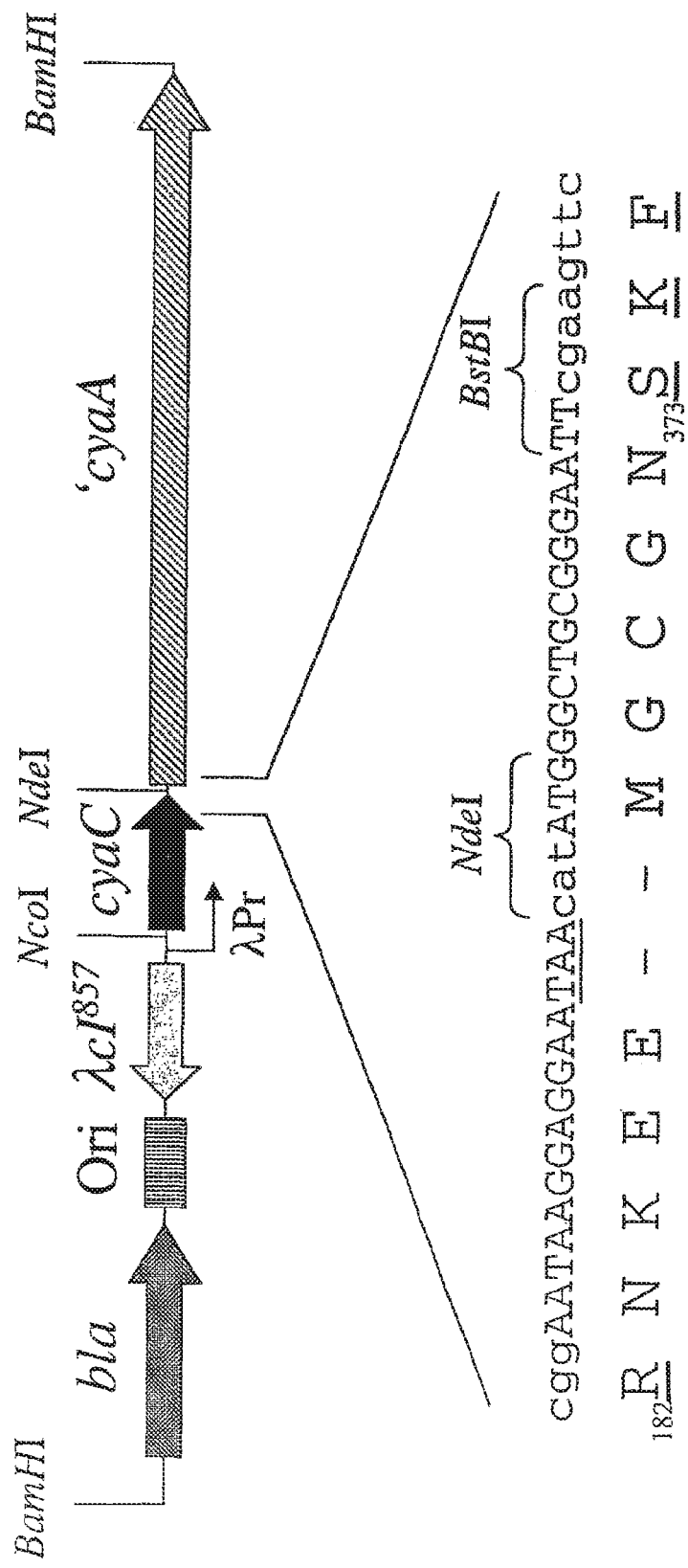

FIG. 16: Schematic representation of pTRAC-373-1706 expression vector.

The large arrows represent the open reading frames of β-lactamase (bla), the thermosensitive repressor cI$^{857}$ of phage lambda (λcI$^{857}$), the cyaC gene and truncated 'cyaA gene (the arrows are pointing to the direction of translation of the corresponding genes). The ColE1 origin (Oil), the Pr promoter (APr), and some relevant restriction sites are also indicated. The intergenic region between the cyaC and truncated 'cyaA genes is detailed in the lower part. It shows the new C-terminus extension of cyaC (downstream to Arg182 of wild-type CyaC), the stop codon (underlined), the initiator Met and first codons of CyaA373-1706 (upstream to Ser373 of wild-type CyaA).

EXAMPLES

A. The *Bordetella* Adenylate Cyclase Toxin Interacts Specifically with the $\alpha_M\beta_2$ Integrin (CD11b/CD18

A.1 Materials and Methods

A.1.1 Recombinant Toxins and Antibodies

Protocol for CyaA production has already been described elsewhere [Karimova, et al, 1998]. CyaA toxins were produced in *E. coli* BLR strain harboring an expression plasmid, pCACT3, which carries the cyaA structural gene CyaA under the lacUV5 promoter and the cyaC accessory gene required for activation of the protoxin. After solubilization in 8M urea, Hepes-Na 20 mM, pH 7.5, CyaA was purified to more than 95% homogeneity (as judged by SDS-gel analysis, not shown) by sequential DEAE-Sepharose and Phenyl-Sepharose. A recombinant detoxified CyaA toxin, CACTE5-Cys-Ova, harboring a unique cysteine inserted within the genetically inactivated catalytic domain was constructed by inserting an appropriate double strand oligonucleotide between the BsiwI and KpnI sites of pCACT-Ova-E5 [Guermonprez et al, 2000]. In the resulting protein CACTE5-Cys-Ova, the amino acid sequence ASCGSIIN-FEKLGT is inserted between residues 224 and 225 of CyaA. The recombinant toxin was expressed and purified as previously described. The purified protein was labeled on its unique Cys with the highly specific sulfhydryl reagent N-(6-(Biotinamido)hexyl))-3'-(2'-pyridyldithio)propionamide (Biotin-HPDP, PIERCE) according to the manufacturers instructions. The biotinylated-CyaA was re-purified on DEAE-Sepharose to remove the unreacted Biotin-HPDP reagent. Toxin concentrations were determined spectrophotometrically from the adsorption at 280 nm using a molecular extinction coefficient of 142 $M^{-1} \times cm^{-1}$ (binding studies) or using the Biorad protein assay system (cAMP accumulation and cell death studies).

Purified mAbs specific for murine CD11a (2D7, Rat IgG2a, κ), murine and human CD11b (M1/70, Rat IgG2b, κ), murine CD11c (HL3, Hamster 1, λ), murine CD18 (C71/16, Rat IgG2a, κ), control (A95-1, or anti-CD16/32, 2.4G2, Rat IgG2b, κ) originated from Pharmingen (San Diego, USA). Supernatants from anti-human CD11b (44, Mouse IgG2a, κ), and anti-human CD18 (TS/18, Mouse IgG1, κ) hybridoma were a kind gift and were used at 1/2 dilution in blocking experiments. Supernatants from an anti-murine CD11b (5C6, Rat IgG2b, κ) were a kind gift from G. Milon (Pasteur Institute, Paris) and were used at 1/2 final dilution in binding inhibition assays. Anti-CyaA polyclonal antibodies were obtained from a rabbit immunized subcutaneously with purified CyaA.

Sera were precipitated from immune serum by ammonium sulfate (33%). After centrifugation the pelleted proteins were resuspended in 20 mM Hepes-Na, 150 mM NaCl, pH 7.5 (buffer C) and extensively dialysed against the same buffer. The antibodies were then biotinylated by incubation with Biotin-amidocaproate N-Hydroxysuccinimide ester (SIGMA, dissolved in dimethyl sulfoxide) for 130 min at room temperature. Then, 100 mM ethanolamine, pH 9.0 were added and after 30 min of additional incubation, the mixture was extensively dialysed at 4° C. against buffer C. Biotinylated antibodies were stored at –20° C.

A.1.2 Cells and Culture Media

EL4, J774A.1, LB27.4, THP-1 were obtained from the American Type Culture Collection (ATCC) and were cultured in RPMI 1640 supplemented with 10% fetal calf serum, 100 U/ml penicillin, 100 µg/ml streptomycin, 2 mM L-glutamine, with or without $5 \times 10^{-5}$ M 2-mercaptoethanol (complete medium). FSDC [Girolomoni et al, 1995] were cultured in complete medium. CHO cells transfected for human CD11b/CD18 or CD11c/CD18 or transfected with the vector only were obtained from D. Golenbock (Boston, USA) and cultured in the presence of neomycin as previously described [Ingalls et al, 1998]. Human neutrophils were purified as previously described [Rieu et al, 1992].

A.1.3 CyaA Binding Assays

All binding assays were performed in DMEM 4.5 mg/ml glucose (Life Technologies) without serum in 96 well culture plates (Costar). $2 \times 10^5$ cells/well were incubated for 20 minutes (at 4° C. or 37° C. depending on the experiments) in a 200 µl final volume. In some experiments, cells were preincubated for 20 min at 4° C. in the presence of blocking mAbs in 100 µl final volume. The toxin solution was added to the wells in the continuous presence of the mAbs in a total volume of 200 µl at 4° C. Then, plates were centrifuged at 1500 rpm for 5 min and supernatants were removed. Cells were incubated at 4° C. for 25 minutes with biotinylated anti-CyaA rabbit polyclonal antibodies (1/400 in DMEM, 50 µl/well) in the presence of a control (non-immune or pre-immune) rabbit serum as a saturating agent (1/50).

After centrifugation and supernatant removal, cells were stained with streptavidin-phycoerythrin (PE) (Pharmingen) at 1/300 dilution (50 pt/well). After washing, cells were analyzed by flow cytometry on a FACStar (Becton-Dickinson, Mountain View, USA) in the presence of 5 µg/ml propidium iodide. Gatings were done to exclude cells aggregates and dead cells by propidium iodide exclusion. Experimental points were fitted to a hyperbolic model $\Delta MFI = Bmax*[CyaA]/(K_d+[CyaA])$, with Bmax=% of maximal binding, using the prism software.

A.1.4 cAMP Assay cAMP accumulation was measured by an antigen competition immunoassay [Karimova et al, 1998] in which the incubation medium was composed of DMEM without serum but containing 4.5 mg/ml glucose and 20 U/ml hexokinase. Hexokinase, which catalyzes the ATP-dependent phosphorylation of glucose, was added deplete the extracellular medium for any traces of ATP, thus preventing the extracellular synthesis of cAMP. Therefore, the amount of cAMP measured is representative of the accumulation of strictly intracellular cAMP. $5\times10^5$ cells were preincubated in 96 well plates in 100 µl/well with or without 10 µg/ml of specific mAbs at 4° C. for 1 h and then incubated at 37° C. for 20 min with 0.05, 0.5 or 5 g/ml CyaA and with 10 µg/ml of specific mAbs when present during the preincubation. For the dose response effect of CyaA, cells were directly incubated with the toxin for 20 min at 37° C. After intoxication, cells were centrifuged at 2.500 rpm for 5 min. Samples were lysed with 100 µl of HCl 0.1 N, boiled for 5 min at 120° C., and neutralized with 100 µl of Tris 0.125 M, NaCl 0.2 M. Microtiter plates were coated with cAMP-BSA conjugates diluted at 1/4,000 in $Na_2CO_3$ 0.1 M pH 9.5. They were washed twice in PBS-Tween 0.1%, saturated for 1 h in PBS-BSA 2% and washed five times with PBS-Tween 0.1%. The samples and the CAMP standard (Sigma) were directly added to the plates coated with cAMP-BSA conjugates and serially diluted with a 1/1 mixture of HCl 0.1 N and Tris 0.125 M-NaCl 0.2 M. Anti-cAMP rabbit antibody was added at 1/2,500 in PBS-BSA 2% and incubated at 37° C. for 3 h. Plates were washed five times with PBS-Tween 0.1%. Anti-rabbit antibodies coupled to horseradish peroxidase (Amersham) were added at 1/2,500 in PBS-BSA 2%, incubated at 37° C. for 1 h and revealed using the classical peroxidase reaction. Experimental points of the standard curve were fitted to a sigmoid model using the Prism software.

A.1.5 Toxicity Assay

Cell death was evaluated as previously described [Khelef et al, 1993; Khelef et al, 1995]. Briefly, $10^5$ cells were incubated for 24 hours in a 96 well plate in complete medium and washed once with serum free medium. All cell incubations were further performed in serum free medium. Dose response effects were evaluated by directly applying various concentrations of CyaA to CHO cells at 37° C. for 4 h. For cytotoxicity inhibition, cells were preincubated at 4° C. for 1 h with or without 10 µg/ml of specific mAbs and then incubated at 37° C. with 0.5 µg/ml CyaA for 2 h for J774A.1A.1 cells or with 5 µg/ml for 4 h for CHO cells and with 10 µg/ml of specific mAbs when present during the preincubation. Cell lysis was evaluated using the Cytotox 96™ assay (Promega) which quantifies the amount of lactate dehydrogenase (LDH) released in the medium by dying cells.

A.2 Results

A.2.1 Saturable Binding of CyaA Correlates with the Presence of CD11b at the Surface of Target Cells To characterize CyaA cellular specificity toward a population of leukocytes, we choose three representative murine cell lines expressing various combination of $\beta_2$ integrins: J774A.1, a tumoral macrophage; EL4, a T cell thymoma, and LB27.4, a B cell lymphoma. After a 20 minutes of incubation with CyaA at 37° C., binding of CyaA to the cell surface of these cells was monitored by flow cytometry using biotinylated anti-CyaA antibodies and streptavidine-PE. Under these conditions, we observed an efficient, dose-dependent and saturable binding of CyaA on J774A.1 cell line. The affinity of CyaA for J774A.1 cells was high since the apparent $K_d$ were 9.2±4.5 nM and 3.2±1.9 nM, respectively. A low binding of CyaA to EL4 and LB27.4 cells was observed but it was not saturable at the concentrations tested.

In order to determine if the binding of CyaA to J774 cell lines was correlated to the expression of one of the members of the $\beta_2$ integrin family, we performed a phenotypic analysis of these cells by flow cytometry using monoclonal antibodies (mAbs) specific for the three a chains of the well characterized $\beta_2$ integrins (CD11a, Cd11b and CD11c) and for the common β chain (CD18) (FIG. 1 *b, c, d, e*). J774A.1 cells expressed mostly CD11b and CD18, but were also positive for CD11a. EL4 cells and LB27.4 cells expressed mostly CD11a and CD18. Taken together, these data show that the efficient and saturable binding of CyaA to J774A.1 was correlated with the presence of the integrin CD11b/CD18.

A.2.2 CyaA Saturable Binding is Specifically Blocked by Anti-CD11b mAbs

Figure 2A:
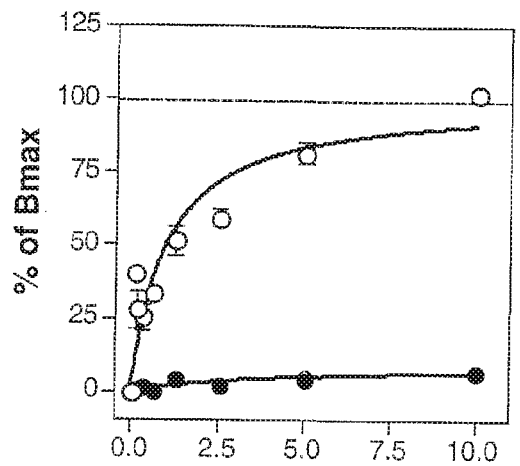
Figure 2B:
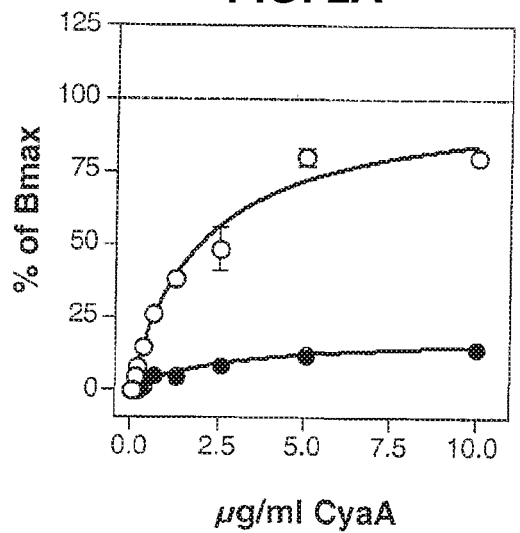
Figure 2C:
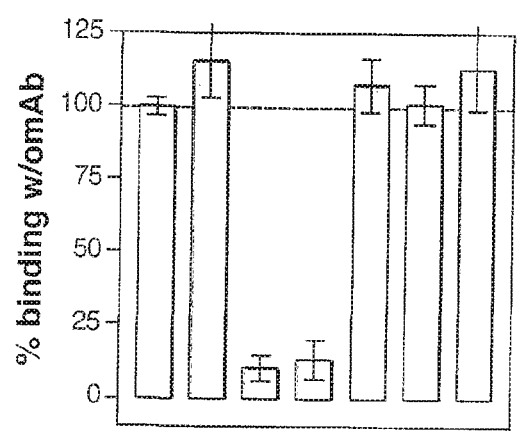
Figure 2D:
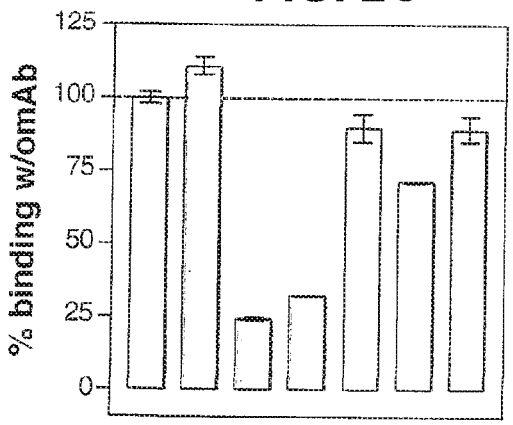

We next examined if CD11b/CD18 could be directly involved in the binding of CyaA to the cells expressing this integrin. We performed a quantitative analysis of inhibition obtained with anti-CD11b M1/70 mAb by calculating percentage of mean fluorescence values in the absence of mAbs at a fixed or varying concentrations of CyaA (FIG. 2). Inhibition of CyaA binding obtained with the M1/70 anti-CD11b mAb was almost total at most CyaA concentrations tested (FIG. 2*a, b*): This inhibition was specific since anti-CD11a, CD11c, CD18 or a control mAb did not inhibit CyaA binding. A second anti-CD11b mAb (done 5c6) also inhibited binding of CyaA (FIG. 2*c,d*). Similar results were obtained with FSDC, an immature dendritic cell line expressing CD11b (FIG. 2*a, c*), and the J774A.1 macrophage cell line (FIG. 2*b, d*).

Figure 3A:
Figure 3B:
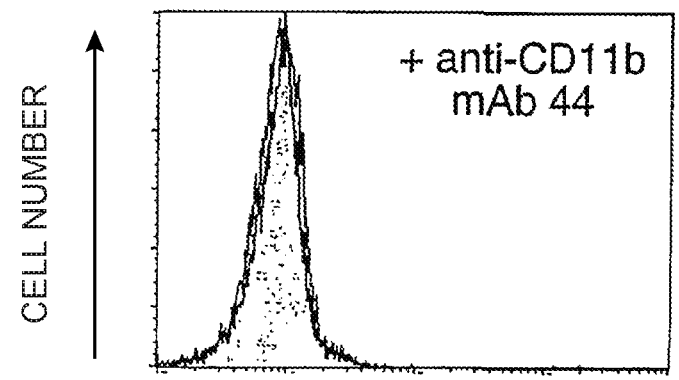
Figure 3C:
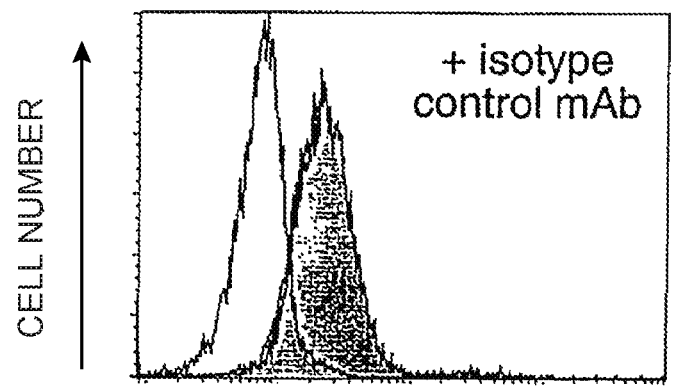
Figure 3D:
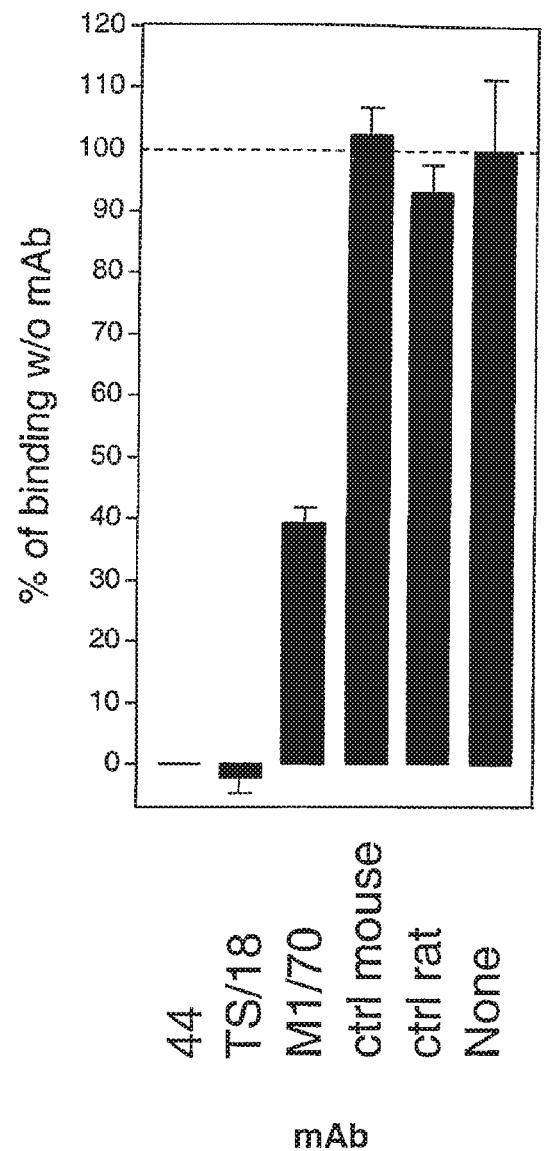

To examine whether CyaA could similarly interact with human CD11b, CyaA binding studies were performed on human neutrophils, whose high expression of CD11b is well established. Since high background fluorescence was obtained following incubation of human myeloid cells with the anti-CyaA rabbit antibodies (data not shown), we set up an alternate binding assay. A detoxified form of CyaA was specifically biotinylated on unique cysteine residues, genetically introduced within its catalytic domain. Using this system, we were able to detect CyaA binding to neutrophils (FIG. 3). Preincubation of neutrophils with the 44 or M1/70 anti-CD11b mAbs led to, a respectively complete or partial inhibition of the binding of CyaA (FIGS. 3*a* and *b*). Unlike the C71/16, anti-murine CD18 mAb that did not block CyaA binding to murine cells, preincubation with the human anti-CD18 TS/18 mAb led to a complete inhibition of CyaA binding to human neutrophils (FIG. 3*b*). Similar results were obtained with the human monocytic THP-1 cell line (data not shown).

In conclusion, CyaA binding to the surface of three myeloid cell lines from both murine and human origin (J774A.1, FSDC, THP-1) as well as freshly purified human neutrophils appears to be mainly mediated through the CD11b/CD18 integrin.

A.2.3 CyaA-Mediated cAMP Increase and Toxicity are Specifically Blocked by an Anti-CD11b mAb To evaluate the physiological relevance of CD11b/CD18-dependent CyaA binding, we studied the effect of blocking mAbs on the cytotoxicity of CyaA. We first measured the amount of cAMP produced in J774A.1 cells exposed to CyaA in the presence of various mAbs. As shown in FIG. 4a, the increase in the intracellular cAMP content induced by CyaA was totally abolished when cells were preincubated with the M1/70 anti-CD11b mAb. The C17/16 anti-murine CD18 mAb had that did not block CyaA cell binding (FIG. 2) had no effect on the intracellular cAMP content of CyaA treated cells. Thus, these data strongly suggest that the increase in intracellular cAMP induced by CyaA is dependent upon the interaction of the toxin with CD11b. To further analyze the requirement of this molecule for the toxicity of CyaA, we evaluated the effect of mAbs specific for the different chains of the $\beta_2$ integrin family on CyaA mediated cell death. FIG. 4b shows that anti-CD11b mAb J774A.1 dramatically reduced the cell death induced by CyaA (88% inhibition). The cell death induced by CyaA was unaffected when J774A.1 were preincubated with mAbs that did not block toxin binding to cells (anti-CD11a, CD11c or CD18 or a control mAb).

Taken together, these data indicate that CyaA binding through CD11b is strictly required for CyaA mediated toxicity in J774A.1 cells.

A.2.4 Transfection of CHO Cells with CD11b/CD18 Confers Sensitivity to CyaA

Figure 5B:
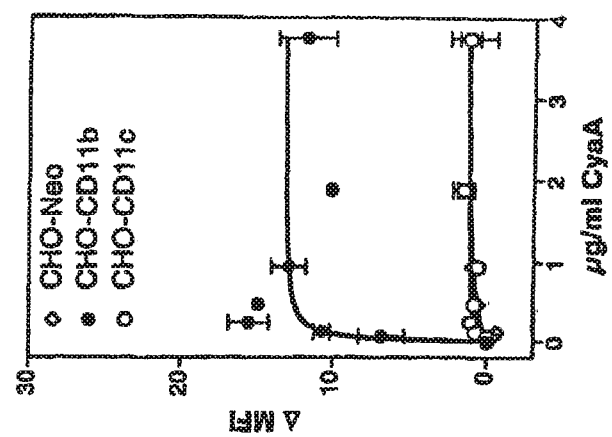
Figure 5A:
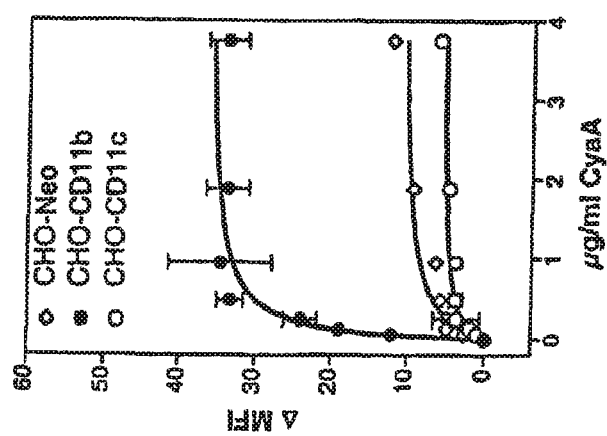

To confirm the role of CD11b in CyaA binding, we used CHO cells transfected with the human integrins CD11b/CD18 or CD11c/CD18 or mock transfected (vector alone). As shown in FIG. 5a, CyaA could bind, at 37° C., to these cell lines. However, CyaA binding was efficient and saturable in CHO cells expressing CD11b/CD18 but not in CD11c/CD18 or mock-transfected cells. The affinity of CyaA for CD11b/CD18 transfected cells was in the nM range (Kd=0.7±0.09 nM). At 4° C., the efficiency of CyaA binding was reduced as compared with the binding at 37° C. (FIG. 5b). At this temperature, the differences between CD11b/CD18 transfected cells and the two other cell lines were more pronounced.

Since we found that CD11b was required for CyaA mediated toxicity in J774A.1, we then determined if CD11b expression was sufficient to confer a CyaA-sensitive phenotype to CHO transfected cells. In line with previous reports [Gordon et al, 1988], CyaA induced a notable amount of intracellular cAMP in CHO cells transfected with CD11c/CD18 or in control mock-transfected cells, but only at high concentrations of toxin (5 µg/ml, FIG. 5c). In contrast, CyaA increased intracellular level of cAMP in CD11b/CD18 transfected CHO cells even at the lowest concentration studied (0.05 µg/ml). Moreover, the cAMP production in response to 5 µg/ml CyaA was 4 to 5 times more elevated in CD11b/CD18 transfected cells as compared to CD11c/CD18- or mock-transfected cells.

Figure 5D:
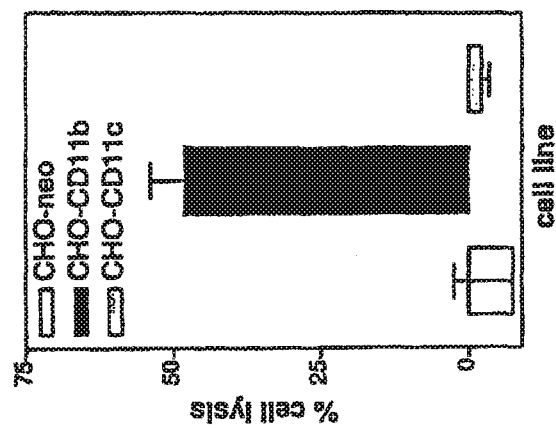
Figure 5C:
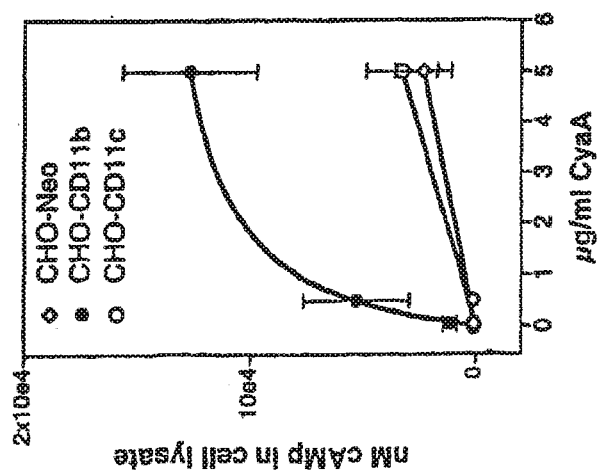

We also evaluated the role of CD11b/CD18 in CyaA-mediated cell death. As shown in FIG. 5d, more than 50% of CHO transfected with CD11b/CD18 were killed after 4 hours incubation with 5 µg/ml of CyaA, whereas CD11c/CD18- or mock-transfected cells were not affected by this treatment.

Altogether, these results thus clearly established that expression of human CD11b/CD18 integrin is sufficient to create a high affinity receptor for CyaA in CHO cells.

A.3 Discussion: A Receptor for CyaA

Unlike other toxins, CyaA has been considered for a long time, as independent of any receptor binding. This is based on the observations that CyaA can intoxicate in vitro a wide variety of model cell lines from various origin [Ladant et al, 1999] ii) CyaA binds to Jurkat cells and sheep erythrocytes in a non saturable fashion [Gray, et al 1999]. In fact, these observations established that non-specific adsorption of CyaA to lipid membranes leads to some translocation of the catalytic domain into the cytosol. However, they did not rule out the existence of a specific receptor. We showed in this study on myeloid cell lines that the binding and the toxic properties of CyaA are dependent on its interaction with the integrin CD11b/CD18. Efficient and saturable binding correlates with the expression of CD11b and is fully and specifically blocked by anti-CD11b mAbs. Moreover, expression of CD11b/CD18 in CHO cells dramatically enhances the binding of CyaA, resulting in an increased sensitivity to intoxication by this toxin. Our results are the first evidence supporting the interaction of CyaA with a cell-surface molecule specifically expressed on leukocytes. The nearly complete blockade of CyaA binding by anti-CD11b mAbs suggests that CD11b is the main receptor for CyaA in the cell lines tested. The lack of efficient binding to CD11c/CD18 transfectants, or CD11a/CD18 expressing cells such as EL4 or LB27.4 suggest that CD11b/CD18 is the only integrin of the β2 family involved in the binding of CyaA to target cells.

In line with previous studies, we observed a detectable binding of CyaA to all cell lines tested. Furthermore, CyaA at high concentrations triggered a small but detectable cAMP increase in mock-transfected CHO cells, that is not associated to cell death. Thus, at high concentration, CyaA can bind and translocate to a wide variety of cell lines but efficient and saturable binding, translocation and killing is a hallmark of CD11b expressing cells.

Binding of CyaA to a member of the β2 integrin family is reminiscent of the behavior of other RTX toxins which were recently found to interact with these molecules [Lally et al, 1997; Li et al, 1999; Ambagala et al, 1999; Jeyaseelan et al, 2000]. The E. coli HlyA, that shares a strong homology with CyaA, forms cationic pores at the plasma membrane. HlyA exhibits a specificity for leukocytes but only at low concentration [Welch et al, 1991]. This relative specificity was shown to be mediated by its interaction with the integrin CD11a/CD18 [Lally et al, 1997]. Similarly, A. actinomycetemcomitans and P. haemolytica leukotoxin (LtxA and LktA, respectively), which are less promiscuous RTX toxins specific for human and bovine leukocytes, respectively, also interact with CD11a/CD18 [Lally et al, 1997; Li et al, 1999; Ambagala et al, 1999; Jeyaseelan et al, 2000]. Despite its strong homology with HlyA, CyaA recognizes another $\beta_2$ integrin (CD11b/CD18) whose cellular distribution is different. Indeed, CD11b is expressed mostly on macrophages, neutrophils and dendritic cells, but not on the majority of T and B cells, whereas CD11a is expressed on all leukocytes including T and B lymphocytes.

This specific targeting of CyaA to CD11b expressing cells is exploited in the present invention to specifically target this particular subset of cells. Detoxified mutants of CyaA remaining invasive could be used for the delivery of pharmacologically active molecules to CD11b positive cells, without noticeably affecting other cell types.

B. Targeted Antigen Delivery to the Cytosol of Myeloid Dendritic Cells and Selective CTL Priming B.1 Materials and Methods B.1.1 Recombinant Adenylate Cyclase Toxins and Peptide The pOVA synthetique peptide (SIINFEKL) originated from NEOSYSTEM and was diluted in PBS at 1 mg/ml.

B.1.2 Immunization and Assay for the Detection of Cytotoxic T Cells

Female C57BL/6 (H-$2^b$) from Iffa Credo (L'arbresle, France) were used between 6 and 8 weeks of age. TAP1-/- (Van Kaer et al., 1992), CD4-/- (Killeen et al., 1993), CD40-/- (Kawabe et al, 1994) and B cell deficient NMT (Kitamura et al, 1991) bred onto a C57BL/6 background originated from the CDTA facility (CNRS, Orleans, France) and were bred in the Institut Pasteur facilities. Animals were intravenously immunized with Ag in PBS. Seven days post-injection, animals were sacrificed and the spleen was removed. Single cell suspensions of splenocytes ($2.5 \times 10^7$ cells) were restimulated in 10 ml CM (see below) with irradiated spleen cells ($2.5 \times 10^7$ cells) for 5 days in the presence of 1 µg/ml pOVA. Cytotoxicity assay was performed exactly as previously described (Fayolle, et al., 1999).

B.1.3 Cell Lines

B3Z (Karttunen et al., 1992), a CD8+ T cell hybridoma specific for the OVA 257-264 peptide (SIINFEKL) in the context of H-$2K^b$ was a generous gift from Dr N. Shastri (University of California, Berkeley, USA).

B.1.4 Antigen Presentation Assays

All antigen presentation assays were performed by coculture of APC with B3Z in 96 well culture microplates (0.2 ml final volume) in RPMI 1640 supplemented with 10% Fetal Calf Serum, 100 U/ml penicillin, 100 µg/ml streptomycin, 2 mM L-glutamine, and $5 \times 10^5$M 2-mercaptoethanol (complete medium, CM). The stimulation of B3Z cells ($10^5$ cells/well) was monitored by IL-2 release in the supernatants of 18-24 hours cultures in the presence of APC. IL-2 was measured in CTLL assay as previously described (Guermonprez et al., 1999). In some experiments (see figure legends), B3Z stimulation was assessed using the NF-AT lacZ reporter assay. LacZ activity in cell lysates was assessed with the CPRG substrate as previously described (Karttunen et al., 1992). Two antigen presentation assays were performed: i) In vitro assay: APC originated from naive mice were cocultured ($10^5$/well) with B3Z in the presence of Ag at various concentrations. In some experiments, APC were preincubated or not with mAbs at 10 µg/ml for 40 minutes at 4° C., then Ag was added to the cells in a 100 µl final volume in the continuous presence of the mAbs. After a 4 hours pulse, APC were washed twice and put in coculture with B3Z. Purified mAbs used were against CD11b (M1/70 ratIgG2b, K) or isotype-matched control and originated from Pharmingen (San Diego, USA). ii) Ex vivo assay: APC originated from mice previously intravenously immunized with various Ags and were put in culture with B3Z in a 0.2 ml final volume at various numbers of APC per well.

B.1.5 Antigen Presenting Cells and Sortings

Total spleen cells (TSC), low density (LDF) and high density (HDF) fractions were prepared according to the protocol of Steinman modified by Vremec et al. (Vremec et al., 1992). Briefly, spleens were digested with collagenase for 40 minutes at 37° C. and then dilacerated and prepared in the continuous presence of EDTA 5 mM. Cells were centrifugated on a dense BSA solution. Supernatant and pellet cells were collected apart and termed low density and high density fractions. CD11c staining was performed at 4° C. in PBS supplemented with 5% of Fetal Calf Serum and 2 mM EDTA (PBS-FACS) with the hamster HL3 mAb coupled to phycoerythrin (PE), fluoresceine isothyocyanate (FITC) or biotinylated and then revealed by Streptavidine-PE. CD8a staining was performed with the 53-6.7 mAb coupled to PE. CD11b staining was performed with the M1/70 mAbs coupled to PE or FITC. CD54R staining was performed with the B220 mAb coupled to PE or biotinylated and revealed by streptavidine-PE. All mAbs originated from Pharmingen. After two washes, cells were sorted using a FACStar (Beckton Dickinson, Mountain View, USA). Cells were aseptically recovered in CM. Purity of the sorted cells was checked on an aliquot of the sorted cells analyzed on a FACScan apparatus (Beckton Dickinson, Mountain View, USA). Purity of the sorted cells was typically between 80 and 98%. In other experiments (as mentioned in figure legends), CD11c+ cells were sorted directly from spleen collagenase digests using the CD11c Micro Beads and the Magnetic Cell Sorting technology following the supplier protocole (MACS, MiltenyiBiotec, Bergish Gladbach, Germany). Purity of the sorted cells ranged around 80% with this technique.

B.2 Results

Figure 6D:
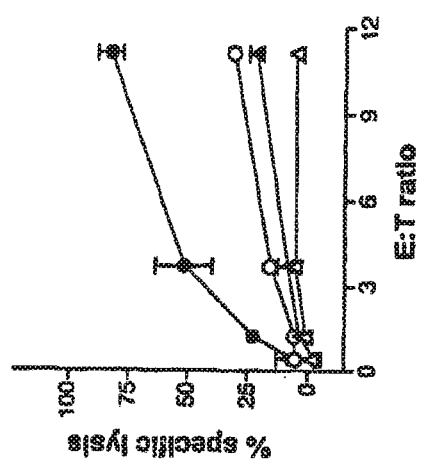
Figure 6C:
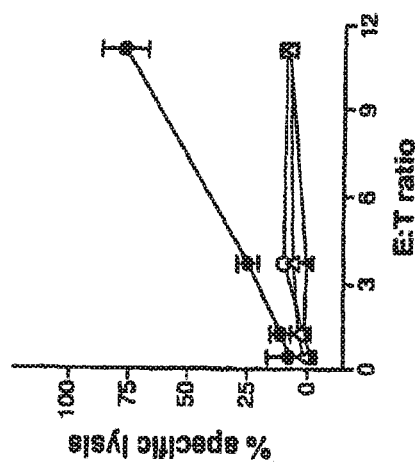

B.2.1 CD4- and CD40-Independent CTL Priming after Systemic Immunization with CyaAOVA in the Absence of Adjuvant The chicken ovalbumin, H-$2K^b$ restricted, SIINFEKL epitope was used as an experimental model epitope. It was genetically inserted in the catalytic domain of a detoxified, still invasive mutant CyaA. C57BL/6 (H-$2^b$) mice were immunized iv once with 50 µg of the recombinant toxin or control saline solution. Seven days after immunization, CTL activity specific for pOVA was detected within splenocytes of CyaAOVA-immunized C57BL/6 mice but not in mice injected with saline or a control CyaA (FIG. 6a). Similar results were obtained with CD4 or CD40 deficient mice indicating that, unlike many other CTL responses (as those raised against cross-priming Ag (Bennett et al, 1997; 1998; Schoenberger et al., 1998, Ridge et al., 1998) CD4+ T cell help was not mandatory for priming of CTL responses by CyaAOVA (FIG. 6b, c). Furthermore, B cells were not required since CTL responses were also obtained in B cell deficient mice (IgM-/-, FIG. 6d). Contaminant LPS, possibly acting as adjuvants, are not involved in the stimulation of CTL responses CyaAOVA since C57BL10ScSn and the LPS-hyporesponsive mice C57BL10ScCr displayed similar OVA-specific CTL response after CyaAOVA injection (not shown).

B.2.2 In Vitro and In Vivo Targeting of CyaAOVA Presentation to CD11b-Expressing Cells In order to better understand the immunogenicity of CyaAOVA, we intended to determine the APC involved in its presentation to CD8+ T cells. Using the IL-2 secretion as a readout for stimulation, we show that B3Z, an H-$2K^b$-restricted, anti-OVA T cell hybridoma, is stimulated in vitro by bulk splenocytes in the presence of CyaAOVA but not CyaALCMV (FIG. 7a). We intended to analyze the APC ability of three well defined splenic APC: DC (CD11c+), B cells (CD45R+) and macrophages/granulocytes (CD11b$^{high}$+ CD11c-). Due to the low percentage of CD11c+ in total splenocytes (<1%), we performed density fractionation and sorted the CD11c+ from the DC-enriched (4-10%) low density population by flow cytometry. The high density fraction contained only trace amounts of CD11c+ cells. In contrast, the distribution of CD45R+ and CD11b$^{high+}$CD11c− (composed of granulocytes/macrophages) cells in both fractions allowed sortings on the total population for these markers. As shown in FIG. 7b, CyaAOVA was presented most efficiently by DC, less efficiently by CD11b$^{high+}$CD11c and B cells. This correlates with a quasi exclusive distribution of antigen presenting ability within the low density fraction of splenocytes (FIG. 7a). In sharp contrast, both high and low density fractions were able to stimulate B3Z in response to pOVA (not shown).

To detect K$^b$-OVA complexes formed in vivo after immunization, the APC prepared from mice iv immunized 8-15 hrs before with 50 μg CyaAOVA were cocultured with B3Z in vitro without Ag addition (ex vivo assay). As for in vitro assays, APC responsible for CyaAOVA presentation were present exclusively in the DC-enriched low density fraction of splenocytes (FIG. 7e). The specificity of the assay was checked with APC from CyaALCMV-immunized mice that did not stimulated B3Z (FIG. 7e). In order to further characterize the low density APC involved in CyaAOVA presentation, we performed cell sortings: results shown in (FIG. 7f) show that DC (CD11c+) fraction was the more efficient APC. The macrophage/granulocyte (CD11b$^{high+}$CD11c−) and the B cells (CD45R+) sorted from the same fraction were very inefficient for the stimulation of B3Z.

To further characterize APC involved in CyaAOVA, we performed subfractionation of the splenic low density CD11c+ DC in CD11c+CD8α− myeloid subset and CD11c+CD8α+ lymphoid subset. In vitro and ex vivo assays FIGS. 7c and g, respectively) showed that antigen presenting ability for CyaAOVA was retained by the myeloid subset that also expressed CD11b+, unlike the lymphoid subset expressing low levels of this integrin (Pulendran et al., 1997; Vremec et al., 1997). The inability of the CD11c+CD8α+ lymphoid subset to present CyaAOVA was specific for CyaAOVA since CD11c+CD8α+ and CD11c+CD8α− presented equally well the pOVA synthetic peptide to B3Z.

In vitro and ex vivo assays performed with splenocytes from control (C57BL/6) or B cell-deficient mice (IgM−/−) confirmed the poor contribution of B cells to CyaAOVA presentation in vitro and in vivo (FIGS. 7d and h). In line with these results, CTL responses induced by CyaAOVA were not significantly affected in B cell-deficient mice as compared to control mice (FIG. 5d).

B.2.3 MHCI-Restricted Presentation of CyaAOVA by Dendritic Cells Depends on the Cytosolic Delivery of the Recombinant Toxin Both in Vitro and In Vivo To determine whether CyaAOVA presentation depends on the cytosolic delivery of the OVA epitope or extracellular loading, we performed Ag presentation assays with total splenocytes or CD11c+ DC from TAP−/− or control TAP+/+ splenic purified from naive animals (in vitro, FIG. 8a) or from animals immunized iv with CyaAOVA (ex vivo, FIG. 8b). Results show that CyaAOVA presentation by dendritic cells is fully dependent on TAP either in vitro or in vivo. Since pOVA presentation is a TAP-independent phenomenon, we checked the functionality of TAP−/− DC sorted from CyaAOVA-immunized mice by stimulating B3Z with these cells loaded in vitro with the pOVA peptide (not shown). These results show that in vivo presentation of CyaAOVA depends on its cytosolic delivery.

B.2.4 Interaction of CyaA with CD11b is Required for Cell Binding and Delivery of the Inserted Antigen to the Cytosolic Pathway for Antigen Presentation by MHC I We showed on part A that saturable and efficient binding of CyaA WT to CD11b+ cells can be blocked specifically by anti-CD11b mAbs. Moreover, CD11b transfection specifically conferred saturable binding and sensitivity to CyaA WT to otherwise CD11b− cells resistant to CyaA WT. Cell binding blockade by anti-CD11b mAbs inhibited subsequent intracellular delivery of the catalytic adenylate cyclase domain, cAMP elevation and cell death induced by CyaA WT. Since this results have been obtained on cell lines, it remained to determine if CyaA binds to splenocytes. We set up a flow cytometric assay to detect the fixation of a biotinylated, detoxified form of CyaA carrying the OVA peptide (CyaAOVAbiotine) to total splenocyte suspensions with streptavidin coupled to phycoerythrin. Using this assay, we observed that CyaAOVA binds to a subset of leukocytes within the total splenocyte suspension (5-7%). Preincubation with the anti-CD11b M1/70 mAb but not a control mAb abrogated this binding (FIGS. 9A-E). Furthermore, there is a correlation between the expression of CD11b and CyaAOVA binding to low density cells: CyaAOVA binds efficiently to CD11c+CD8α− that expresses high levels of CD11b, less efficiently to CD11c+CD8α+ that expresses low levels of CD11b and very weakly to CD11c−CD8α+ T cells that do not express CD11b (FIGS. 9F-J). It is noticeable that CyaOVA binds efficiently to a low percentage of CD11c−CD8α− cells in correlation with the presence of CD11b$^{high+}$ into this CD11c− population. Thus, CyaOVA biotine binding is mediated by CD11b (as for CyaA WT) and predicts the ability of a given cell type to present CyaOVA.

In vitro, we showed that the anti-CD11b mAb M1/70 blocks the CyaAOVA presentation by TSC cells to B3Z (FIG. 10a). This blockade is specific since i) a control mAb or mAbs specific for other β2 integrin family members (anti-CD11a, CD11c) had little or no effect (FIG. 10a and data not shown) ii) the presentation of pOVA was not affected by the anti-CD11b or none of these mAbs (FIG. 10b and data not shown). This confirms that CD11b is the main receptor for CyaAOVA at least in the spleen, and that CyaAOVA-CD11b interaction is mandatory for the presentation of the inserted epitope. Finally, to ascertain the role of CD11b expressing cells in CyaAOVA presentation, we performed sorting experiments on whole splenocyte cells from mice immunized with CyaAOVA or pOVA. Total splenocyte cells were sorted in CD11b+ and CD111a− fractions. Whereas the two subpopulations stimulated B3Z after pOVA iv immunization (FIG. 10d), only the CD11b+ subpopulation stimulated B3Z after CyaAOVA iv immunization (FIG. 10c).

Taken together, these results clearly establish that the presentation of the OVA peptide from CyaOVA is dependent on cell binding and thus on interaction with CD11b.

B.3 Discussion

In the present study, using the detoxified adenylate cyclase of *Bordetella pertussis* as an epitope-delivery vector, we established a strategy for immunization that primes CTL responses after a single injection, bypassing the need for adjuvant requirement. We identified mechanisms that contribute to the high efficiency of detoxified CyaA as a vector:

B.3.1 CyaA Target Myeloid Dendritic Cells Through its Interaction with the CD11b Integrin Antigen presenting assay to a specific CD8+ T cell hybridoma using in vitro- or in vivo-loaded APC (in vitro and ex vivo assay, respectively) demonstrated that the most efficient APC for CyaAOVA are CD11c+CD11b$^{high+}$ DC. Indeed, all the Ag presenting ability for CyaAOVA belonged to the low density fraction of splenocytes that retains DC. Cell sorting of defined cell types revealed that CD11c+

CD11b$^{high+}$ DC cells are much more efficient than CD11c$^-$ CD11b$^{high+}$ cells to present CyAOVA. The minor contribution observed for B cells (CD45R$^+$) was confirmed by efficient presentation of CyaAOVA (in vitro and ex vivo) and CTL responses in B cell-deficient mice.

B.3.2 CyaA Delivers Ag to the Cytosolic Pathway for MHC Class I Presentation In Vivo Here we show the dependence of CyaAOVA presentation to total splenocytes in vitro. Strikingly, we also show that in vivo presentation of CyaAOVA takes also place according a TAP-dependent pathway. This lead to the conclusion that CyaAOVA presentation in vivo resulted effectively from cytosolic delivery and not from an eventual extracellular degradation.

B.3.3 CTL Priming Bypass CD4+ T Cell Help and is Independent on CD40 Signaling

Maturation from an immature stage toward a mature stage is characterized by i) a decrease in Ag capture ability, ii) an increase in T cell priming ability, iii) a migration from Ag sampling sites (marginal zone in the spleen) toward T cell area (peri arteriolar sheets in the spleen) were they maximize the probability of encounter with Ag-specific T cells (De smedt et al., 1996). In addition to Ag presentation by DC, the maturation phase is now widely assumed as a prerequisite for T cell priming. In vitro studies have highlighted the role of CD4$^+$ T cells in signalling DC maturation, notably via CD40L-CD40 interaction (Bell et al., 1999). In the case of CD8+ T cells priming after the cross priming of cellular Ag, CD4$^+$ T cells dispensate their help to CD8+ T cells in a CD40-dependent mechanism (Schuurhuis et al., 2000; Bennett et al., 1998; Schoenberger et al., 1998; Ridge et al., 1998). Since CyaAOVA primes CTL in a CD4 and CD40 independent way, it is tempting to speculate that detoxified CyaA could be endowed of intrinsic adjuvanticity.

B.3.4 Conclusion

The present study represents the first characterization, to our knowledge, of a proteinaceous vaccine vector that fits both targeting to professional APC, cytosolic delivery of the vectorized Ag and adjuvant-free CTL priming. Moreover, we elucidated the mechanism of cell targeting by demonstrating that Ag presentation is dependent on the interaction between CyaA and CD11b, its receptor. Hence, the cellular specificity of CyaA is serendipituously adapted to the Ag delivery purpose. Finally, the cellular specificity of CyaA or other bacterial toxins may serve the cytosolic delivery of a wide set of pharmaceutically-relevant molecules whose effects should be targeted on a restricted set of cells.

C. Use of Adenylcyclase to Deliver Chemically Coupled Antigens to Dendritic Cells In Vivo C.1 Methods for Coupling Molecules of Interest to CyaA-Derived Vectors A general methodology is here described to create recombinant CyaA toxins by grafting molecules of interest to CyaA by means of disulfide bonds.

As an illustration, a synthetic 12 amino-acid long peptide corresponding to a CD8$^+$ T-cell epitope from ovalbumin was chemically crosslinked through a disulfide bond to a cysteine residue genetically introduced into the CyaA catalytic domain at position 235 (wild type CyaA has no cysteine residues). The expected advantages of this novel architecture are:

(i) versatility: a single CyaA carrier protein can be easily coupled to any desired synthetic peptides;

(ii) immunogenicity: upon delivery into the APC cytosol, the epitopes chemically coupled to CyaA should be released from the vector (due to the reducing intracellular conditions) and introduced directly into the MHC class I presentation pathway, thus bypassing the potentially limiting step of proteolytic processing by proteasome.

The general procedure to couple synthetic peptides to CyaA by disulfide bonds is outlined in FIG. 11.

In a first step, a recombinant CyaA toxin that contains a single cysteine residue genetically inserted within the catalytic domain of CyaA (wild type CyaA has no cysteine residue) is produced.

The recombinant CyaA toxin, ACTM235, has been previously characterized (Heveker and Ladant, 1997). In particular, ACTM235 harbors a Cys-Ser dipeptide inserted between amino-acid 235 and 236 and is fully cytotoxic. This toxin was expressed and purified to homogeneity as previously described in A.1.1.

In a second step a synthetic peptide corresponding to a CD8$^+$ T cell epitope from ovalbumin was designed: in addition to the SIINFEKL (one letter code for amino acid) sequence that is the precise epitope sequence, a cysteine residue with an activated Nitro-pyridin-sulfonyl thiol group (Cys-NPys) was added at the N-terminus of the peptide during chemical synthesis. The activated Npys-cysteine was separated from the SIINFEKL sequence by a flexible GGA motif to facilitate further proteolytic processing of the peptide within APC. The peptide (Cys-Npys-OVA, molecular weight: 1405 da) was synthesized by Neosystem (Strasbourg, France).

In a third step the Cys-Npys-OVA peptide was coupled to ACTM235 using the following procedure.

Ten mg of purified ACTM235 in 8 M urea, 20 mM Hepes-Na, pH 7.5, were reduced by incubation for 12 hrs in the presence of 10 mM Dithiothreitol (DTT). The efficiency of reduction was checked by an SDS-Page analysis under non reducing conditions: essentially all the ACTM235 protein migrated as a single band of 200 kDa corresponding to the monomeric species without evidence of any dimeric species (molecular weight of about 400 kDa). The reduced protein was then loaded on a DEAE-sepharose (Amersham Pharmacia Biotech) column (5 ml packed resin) equilibrated in 8 M urea, 20 mM Hepes-Na, pH 7.5. The ACTM235 protein was fully retained on the DEAE-sepharose resin that was then extensively washed with 8 M urea, 20 mM Hepes-Na, pH 7.5, 0.1 M NaCl (>100 ml) to remove any traces of DTT (the absence of residual DTT was checked using the classical Ellman's reaction with 5,5'-Dithio-bis-(2-nitrobenzoic acid), DTNB). The reduced ACTM235 protein was then eluted from the DEAE-sepharose resin in 7 ml of 8 M urea, 20 mM Hepes-Na, pH 7.5, 0.5 M NaCl. Three mg (about 2 µmol) of Cys-Npys-OVA peptide were then added to the reduced ACTM235 protein (8 mg, about 45 nmol) and the mixture was incubated for 16 hrs at room temperature. Then, 25 ml of 20 mM Hepes-Na, pH 7.5 and 8 ml of 5 M NaCl were added and this diluted mixture was then loaded on a Phenyl-Sepharose (Amersham Pharmacia Biotech) column (10 ml packed resin) equilibrated in 20 mM Hepes-Na, pH 7.5, 1 M NaCl. The Phenyl-Sepharose resin was washed with 50 ml of 20 mM Hepes-Na, pH 7.5, 1 M NaCl and then with 50 ml of 20 mM Hepes-Na, pH 7.5. The derivatized ACTM235 protein was then eluted in 8 M urea, 20 mM Hepes-Na, pH 7.5. The toxin concentration was determined spectrophotometrically from the absorption at 280 nm using a molecular extinction coefficient of 142,000 $M^{-1} \cdot cm^{-1}$.

The Cys-Npys-OVA peptide was coupled using the same procedure to a second recombinant CyaA toxin, CyaAE5-LCMVgp, which is a detoxified variant (i.e. lacking the enzymatic activity as a result of the genetic insertion of 2 amino acid LQ between residues 188 and 189). This toxin also contains a 15 amino acid long polypeptide sequence (PASAKAVYNFATCGT) inserted between residues 224 and 225 of CyaA and that contains a single Cys residues. The plasmid encoding this recombinant toxin is a derivative of pCACT-ova-E5 (Guermonprez et al. 2000) modified by the insertion between the StuI and KpnI restriction sites of an appropriate synthetic double stranded oligonucleotide encoding the PASAKAVYNFATCGT sequence. The CyaAE5-LCMVgp protein was expressed and purified as described previously in A.1.1.

The peptides shown in table 1 were also coupled similarly to another detoxified recombinant CyaA toxin, CyaAE5-CysOVA, which contains the same LQ dipeptide insertion in the catalytic site and a 14 amino acid sequence inserted between residues 224 and 225 of CyaA. This insert contains a Cys residue adjacent to the OVA epitope as shown in FIG. 12. The plasmid encoding this recombinant toxin is a derivative of pCACT-ova-E5 modified by the insertion between the BsiWI and KpnI restriction sites of an appropriate synthetic double stranded oligonucleotide encoding the ASCGSIINFEKLGT sequence. The CyaAE5-CysOVA protein was expressed and purified as described previously in A.1.1.

The CyaAE5-CysOVA can be considered as a general detoxified vector for chemical coupling of CTL epitopes by disulfide bridges. The presence of the OVA epitope within CyaAE5-CysOVA allows for an easy in vitro assay for functionality in epitope delivery by measuring the presentation of the OVA epitope to specific T-cell hybridoma as described previously in B.1.4.

TABLE 1

NPys CTL peptides coupled to CyaAE5-CysOVA

| Name of epitopes | Amino-acid sequence of peptides |
|---|---|
| CEA 571 | Cys(NPys)-GGYLSGANLNL |
| Gp100 | Cys(NPys)-GGITDQVPFSV |
| MelanA | Cys(NPys)-GGEAAGIGILTV |
| Tyrosinase | Cys(NPys)-GGYMDGTMSQV |

Alternatively, the thiol groups of recombinant CyaA toxins can be activated with 2,2'-dithiodipyridine (Sigma) and derivatised with peptides containing a reduced cysteine (the procedure to reduce the Cys in synthetic peptides is provided by the manufacturer). This would be especially appropriate if the desired peptide contains an internal cysteine residue.

C.2 Analysis of the In Vitro and In Vivo Immunogenicity of the OVA Epitope Chemically Coupled to CyaA In vitro delivery of the OVA epitope to MHC class I molecules by CyaA after chemical (CyaA-gp-S-S-OVA E5) or genetic coupling (CyaA-OVA E5) was first analysed by studying the presentation of these molecules to the anti-OVA B3Z CD8$^+$ T cell hybridoma by splenocytes. 3·10$^5$ spleen cells from C57BL/6 mice were co-cultured for 18 h with 10$^5$ B3Z cells in the presence of various concentrations of the recombinant CyaA. The IL-2 release by B3Z was measured in a CTLL proliferation assay.

As shown on the FIG. 13, a high IL-2 secretion was observed when B3Z was stimulated either with CyaA-gp-S-S-OVA E5 or CyaA-OVA E5, thus demonstrating that the OVA epitope chemically linked to CyaA was as efficiently delivered to the cytosolic pathway of the antigen-presenting cells than after genetic coupling. No IL-2 production was observed when B3Z was stimulated with CyaA molecules lacking the OVA epitope, thus showing the specificity of the IL-2 production.

In a second step, in vivo capacity of these molecules to induce OVA-specific CTL responses was then analysed. C57BL/6 mice (2 per group) were immunized by i.v. injection of 50 µg of the various CyaA. Seven days later, 25·10$^6$ spleen cells of individual mice were restimulated with 0.1 µg of OVA peptide in the presence of 25·10$^6$ irradiated syngenic spleen cells for five days. The cytotoxic activity of the effector cells was measured on 51 Cr-labeled EL4 target cells pulsed or not with 50 µM of the OVA peptide.

As shown in FIG. 14, high CTL responses were induced in mice immunized by either CyaA-gp-S-S-OVA E5 or CyaA-OVA E5, thus demonstrating the comparable efficacy of chemical or genetic coupling of the OVA epitope. No CTL response was observed in mice immunized with the control CyaA molecules lacking the OVA epitope or when uncoated EL4 were used as target cells, thus showing the specificity of the CTL responses observed.

In conclusion, these results clearly demonstrate that a CD8$^+$ T cell epitope chemically linked to CyaA-derived proteinaceous vectors is very efficiently delivered to the cytosolic pathway for MHC class I presentation and induces strong CTL response in vivo.

D. Identification of a CyaA-Derived Fragment that Binds to CD11b/CD18 and can be Used as Efficient Molecule Delivery Vectors As an attempt to map the region that is involved in the interaction between CyaA and the CD11b/CD18 receptor, various subfragments of CyaA were constructed and tested for their ability to compete with a biotinylated CyaA toxin for binding to CD11b/CD18 on the surface of transfected CHO cells, using methods previously described in paragraph A.

D.1 Expression of CyaA373-1706

CyaA373-1706 protein was produced in E. coli by using a novel expression vector pTRAC-373-1706 (FIG. 16). It is a derivative of plasmid pDL1312 (Ladant 1995), constructed by replacing the neurocalcin gene of plasmid pDL1312 by the cyaC gene (that encodes CyaC which is involved in the conversion of proCyaA into the active toxin by post-translational palmitoylation of Lys 860 and 983 of CyaA) and the 3' part of the cyaA gene that encodes the C-terminal domain—codons 373 to 1706—of CyaA (see FIG. 16). Both cyaC and 'cyaA genes are placed in the same transcriptional unit under the control of the λ phage Pr promoter. The 3' end of the cyaC gene was modified to introduce before its stop codon, a ribosome binding site to enhance the translation initiation of the downstream 'cyaA gene (FIG. 16). The resulting modification of the CyaC polypeptide (the last 3 amino acid Gly-Thr-Ala at the C-terminus of CyaC were replaced by the Asn-Arg-Glu-Glu sequence) had no effect on its ability to acylate CyaA. The 5' end of the cyaA gene (coding for the catalytic domain of the toxin (upstream of the unique BstBI site of cyaA) was deleted and replaced by an appropriate synthetic double stranded oligonucleotide encoding the MGCGN sequence (FIG. 16).

The pTRAC-373-1706 also encodes the thermosensitive λ repressor CI$^{857}$ that strongly represses gene transcription at the λ Pr promoter at temperatures below 32° C., the origin of replication of colE1 and the beta-lactamase gene that confers ampicillin resistance.

Expression of the CyaA373-1706 protein was carried out in *E. coli* strain BLR. Cells transformed with pTRAC-373-1706 were grown at 30° C. in LB medium containing 150 mg/L of ampicillin until mid-log phase and then synthesis of CyaC and of the truncated CyaA was induced by increasing the growth temperature to 42° C. Bacteria were harvested after 3-4 hrs of further growth at 42° C. CyaA373-1706 protein was then purified as described for the wild type CyaA (Guermonprez et al. 2000). CyaA373-1706 is devoid of cAMP synthesizing activity, it exhibits hemolytic activity of sheep erythrocytes and contains also a unique cysteine residues in its MGCGN N-terminal sequence.

D.2 Inhibition of CyaA-E5 Binding to CD11b by CyaA-E5 and CyaA Fragments: 1-383 (Catalytic Domain) and 373-1706 (Hydrophobic and Repeat Domains)

As shown on FIG. 15, a strong inhibition of biotinylated CyaA-E5 binding was achieved after incubation of transfected CHO cells with CyaA-E5. A similar inhibition was obtained after incubation of these cells with the fragment CyaA-373-1706 whereas CyaA 1-383 had no significant effect on the binding of the biotinylated CyaA-E5.

Thus, these results clearly demonstrate that the fragment of CyaA that encompasses residues 373 to 1706, CyaA373-1706, contains the structures essentially required for the interaction of CyaA with the CD11b/CD18 receptor.

E. Conclusions

Since MHC class I molecules usually present peptides derived from endogenously synthesized proteins, epitopes must be delivered to the cytosol of antigen presenting cells to elicit CTL responses. It has been previously established that the CTL priming activity of recombinant ACT protein relies at least in part on its ability to deliver $CD8^+$ T cell epitopes into the cytosol of antigen-presenting cells (APC). In one approach, epitopes were genetically inserted within the catalytic domain of CyaA as it is known that, for the wild-type toxin, this part of the polypeptide reaches the cytosol of target cells where it exerts its toxic effect (i.e. cAMP synthesis). After entering the cells, the CyaA catalytic domain harboring the epitope insert must be proteolytically processed to release the matured CD8+ T cell epitope which then will be translocated to the endoplasmic reticulum to associate with MHC class I molecules.

This proteolytic processing, carried out by the proteasome, might be a limiting step in numerous cases (Pamer and Cresswell, 1998; Cascio et al., 2001), leading to a significant decrease of the overall yield of the mature epitope. The alternative approach, described here, that consist in the linkage of the epitopes to the catalytic domain of CyaA by means of a disulfide bond, offers a significant advantage in that, with this design, matured epitopes (requiring only N-terminal triming) will be quantitatively released from CyaA inside the cytosol of APC. In addition, this should be a very versatile system as a single CyaA carrier protein could be easily and rapidly coupled to any desired synthetic peptide. Furthermore, it will be easy to introduce by genetic engineering, several cysteine residues within the catalytic domain (such as in previously mapped permissive sites, WO 93/21324 (INSTITUT PASTEUR)) of a recombinant detoxified CyaA toxin so that multiple peptides can be coupled on the same CyaA molecule. This should increase the overall epitope delivery and immunogenicity of the recombinant protein.

Deletion mapping allowed to identify the C-terminal part of CyaA (aa 373-1706) as the region that is involved in the interaction of the toxin with its CD11b/CD18 receptor. The truncated protein CyaA373-1706 can be therefore used as a protein module to target $CD11b^+$ cells in vivo. In particular, polypeptides or proteins corresponding to antigens of interest can be genetically fused to CyaA373-1706 to be delivered to dendritic cells in order to elicit specific immune responses. Similar coupling can be performed on the recombinant CyaA373-1706 protein that also contained a unique cysteine at its N terminal end.

BIBLIOGRAPHY

1. Aichele, P., D. Kyburz, P. S. Ohashi, B. Odermatt, R. M. Zinkernagel, H. Hengartner, and H. Pircher. 1994. Peptide-induced T-cell tolerance to prevent autoimmune diabetes in a transgenic mouse model. *Proceedings of the National Academy of Sciences of the United States of America* 91, no. 2:444-8.
2. Aichele, P., K. Brduscha-Riem, R. M. Zinkernagel, H. Hengartner, and H. Pircher. 1995. T cell priming versus T cell tolerance induced by synthetic peptides. *Journal of Experimental Medicine* 182, no. 1:261-6.
3. Ballard, J. D., R. J. Collier, and M. N. Starnbach. 1996. Anthrax toxin-mediated delivery of a cytotoxic T-cell epitope in vivo. *Proceedings of the National Academy of Sciences of the United States of America* 93, no. 22:12531-4.
4. Bassinet, L., P. Gueirard, B. Maitre, B. Housset, P. Gounon, and N. Guiso. 2000. Role of adhesins and toxins in invasion of human tracheal epithelial cells by *Bordetella pertussis*. Infect Immun 68, no. 4:1934-41.
5. Bell, D., J. W. Young, and J. Banchereau. 1999. Dendritic cells. Advances in Immunology 72:255-324.
6. Bennett, S. R., F. R. Carbone, F. Karamalis, J. F. Miller, and W. R. Heath. 1997. Induction of a CD8+ cytotoxic T lymphocyte response by cross-priming requires cognate CD4+ T cell help. Journal of Experimental Medicine 186, no. 1:65-70.
7. Bennett, S. R., F. R. Carbone, T. Toy, J. F. Miller, and W. R. Heath. 1998. B cells directly tolerize CD8(+) T cells. Journal of Experimental Medicine 188, no. 11:1977-83.
8. Bennett, S. R., F. R. Carbone, F. Karamalis, R. A. Flavell, J. F. Miller, and W. R. Heath. 1998. Help for cytotoxic-T-cell responses is mediated by CD40 signalling [see comments]. Nature 393, no. 6684:478-80.
9. Betsou et al. Infect. Immun. 1993 September, 61(9) 3583-3589.
10. Betsou et al. Infect. Immun. 1995 September, 63(9) 3309-3315.
11. Benz, R., E. Maier, D. Ladant, A. Ullmann, and P. Sebo. 1994. Adenylate cyclase toxin (CyaA) of *Bordetella pertussis*. Evidence for the formation of small ion-permeable channels and comparison with HlyA of *Escherichia coli*. Journal of Biological Chemistry 269, no. 44:27231-9.
12. Carbonetti, N. H., T. J. Irish, C. H. Chen, C. B. O'Connell, G. A. Hadley, U. McNamara, R. G. Tuskan, and G. K. Lewis. 1999. Intracellular delivery of a cytolytic T-lymphocyte epitope peptide by pertussis toxin to major histocompatibility complex class I without involvement of the cytosolic class I antigen processing pathway. Infection & Immunity 67, no. 2:602-7.
13. Casares, S., K. Inaba, T. D. Brumeanu, R. M. Steinman, and C A. Bona. 1997. Antigen presentation by dendritic cells after immunization with DNA encoding a major histocompatibility complex class II-restricted viral epitope. Journal of Experimental Medicine 186, no. 9:1481-6.

14. Condon, C., S. C. Watkins, C. M. Celluzzi, K. Thompson, and L. D. Falo, Jr. 1996. DNA-based immunization by in vivo transfection of dendritic cells. Nature Medicine 2, no. 10:1122-8.
15. Confer, D. L., and J. W. Eaton. 1982. Phagocyte impotence caused by an invasive bacterial adenylate cyclase. Science 217, no. 4563:948-50.
16. Coote, J. G. 1992. Structural and functional relationships among the RTX toxin determinants of gram-negative bacteria. FEMS Microbiol Rev 8, no. 2:137-61.
17. Crowley, M., K. Inaba, and R. M. Steinman. 1990. Dendritic cells are the principal cells in mouse spleen bearing immunogenic fragments of foreign proteins. Journal of Experimental Medicine 172, no. 1:383-6.
18. De Smedt, T., B. Pajak, E. Muraille, L. Lespagnard, E. Heinen, P. De Baetselier, J. Urbain, O. Leo, and M. Moser. 1996. Regulation of dendritic cell numbers and maturation by lipopolysaccharide in vivo. Journal of Experimental Medicine 184, no. 4:1413-24.
19. C. Fayolle, P. Sebo, D. Ladant, A. Ullmann, and C. Leclerc, (1996) In vivo induction of CTL responses by recombinant adenylate cyclase of *Bordetella pertussis* carrying viral CD8(+) T-cells epitopes, J. Immunol. 156.4697-4706
20. Fayolle, C., D. Ladant, G. Karimova, A. Ullmann, and C. Leclerc. 1999. Therapy of murine tumors with recombinant *Bordetella pertussis* adenylate cyclase carrying a cytotoxic T cell epitope. Journal of Immunology 162, no. 7:4157-62.
21. Friedman, R. L., R. L. Fiederlein, L. Glasser, and J. N. Galgiani. 1987. *Bordetella pertussis* adenylate cyclase: effects of affinity-purified adenylate cyclase on human polymorphonuclear leukocyte functions. Infection & Immunity 55, no. 1:135-40.
22. Fuchs, E. J., and P. Matzinger. 1992. B cells turn off virgin but not memory T cells. Science 258, no. 5085:1156-9.
23. Gray, M., G. Szabo, A. S. Otero, L. Gray, and E. Hewlett. 1998. Distinct mechanisms for $K^+$ efflux, intoxication, and hemolysis by *Bordetella pertussis* AC toxin. Journal of Biological Chemistry 273, no. 29:18260-7.
24. Gross, M. K., D. C. Au, A. L. Smith, and D. R. Storm. 1992. Targeted mutations that ablate either the adenylate cyclase or hemolysin function of the bifunctional cyaA toxin of *Bordetella pertussis* abolish virulence. Proceedings of the National Academy of Sciences of the United States of America 89, no. 11:4898-902.
25. Gueirard, P., A. Druilhe, M. Pretolani, and N. Guiso. 1998. Role of adenylate cyclase-hemolysin in alveolar macrophage apoptosis during *Bordetella pertussis* infection in vivo. Infection & Immunity 66, no. 4:1718-25.
26. Guermonprez, P., D. Ladant, G. Karimova, A. Ullmann, and C. Leclerc. 1999. Direct delivery of the *Bordetella pertussis* adenylate cyclase toxin to the MHC class I antigen presentation pathway. Journal of Immunology 162, no. 4:1910-6.
27. P. Guermonprez, C. Fayolle, C. Leclerc, G. Karimova, A. Ullmann, and D. Ladant. (2000) *Bordetella pertussis* adenylate cyclase toxin: a vehicle to deliver CD8+ T-cell epitopes into antigen presenting cells. in Methods in Enzymology, Chimeric Genes and Proteins, 326, 527-542. J. Abelson, S. Emr, and J. Thorner (Eds) Academic Press Inc.
28. Guery, J. C., F. Ria, and L. Adorini. 1996. Dendritic cells but not B cells present antigenic complexes to class II-restricted T cells after administration of protein in adjuvant. Journal of Experimental Medicine 183, no. 3:751-7.
29. Guery, J. C., F. Ria, F. Galbiati, S. Smiroldo, and L. Adorini. 1997. The mode of protein antigen administration determines preferential presentation of peptide-class II complexes by lymph node dendritic or B cells. International Immunology 9, no. 1:9-15.
30. Guiso, N., M. Rocancourt, M. Szatanik, and J. M. Alonso. 1989. *Bordetella* adenylate cyclase is a virulence associated factor and an immunoprotective antigen. Microbial Pathogenesis 7, no. 5:373-80.
31. Guiso, N., M. Szatanik, and M. Rocancourt. 1991. Protective activity of *Bordetella* adenylate cyclase-hemolysin against bacterial colonization. Microbial Pathogenesis 11, no. 6:423-31.
32. Harvill, E. T., P. A. Cotter, M. H. Yuk, and J. F. Miller. 1999. Probing the function of *Bordetella bronchiseptica* adenylate cyclase toxin by manipulating host immunity. Infection & Immunity 67, no. 3:1493-500.
33. N. Heveker and D. Ladant (1997) Characterization of mutant *Bordetella pertussis* adenylate cyclase toxins with reduced affinity for calmodulin. Implications for the mechanism of toxin entry into target cells, Eur. J. Biochem., 243, 643-649.
34. Hewlett, E., and J. Wolff. 1976. Soluble adenylate cyclase from the culture medium of *Bordetella pertussis*: purification and characterization. Journal of Bacteriology 127, no. 2:890-8.
35. Jeyaseelan, S., S. L. Hsuan, M. S. Kannan, B. Walcheck, J. F. Wang, M. E. Kehrli, E. T. Lally, G. C. Sieck, and S. K. Maheswaran. 2000. Lymphocyte function-associated antigen 1 is a receptor for *Pasteurella haemolytica* leukotoxin in bovine leukocytes. Infection & Immunity 68, no. 1:72-9.
36. Karimova, G., C. Fayolle, S. Gmira, A. Ullmann, C. Leclerc, and D. Ladant. 1998. Charge-dependent translocation of *Bordetella pertussis* adenylate cyclase toxin into eukaryotic cells: implication for the in vivo delivery of CD8(+) T cell epitopes into antigen-presenting cells. Proceedings of the National Academy of Sciences of the United States of America 95, no. 21:12532-7.
37. Karttunen, J., S. Sanderson, and N. Shastri. 1992. Detection of rare antigen-presenting cells by the lacZ T-cell activation assay suggests an expression cloning strategy for T-cell antigens. Proceedings of the National Academy of Sciences of the United States of America 89, no. 13:6020-4.
38. Kawabe, T., T. Naka, K. Yoshida, T. Tanaka, H. Fujiwara, S. Suematsu, N. Yoshida, T. Kishimoto, and H. Kikutani. 1994. The immune responses in CD40-deficient mice: impaired immunoglobulin class switching and germinal center formation. Immunity 1, no. 3:167-78.
39. Khelef, N., H. Sakamoto, and N. Guiso. 1992. Both adenylate cyclase and hemolytic activities are required by *Bordetella pertussis* to initiate infection. Microbial Pathogenesis 12, no. 3:227-35.
40. Khelef, N., A. Zychlinsky, and N. Guiso. 1993. *Bordetella pertussis* induces apoptosis in macrophages: role of adenylate cyclase-hemolysin. Infection & Immunity 61, no. 10:4064-71.
41. Khelef, N., and N. Guiso. 1995. Induction of macrophage apoptosis by *Bordetella pertussis* adenylate cyclase-hemolysin. FEMS Microbiology Letters 134, no. 1:27-32.
42. Khelef, N., C. M. Bachelet, B. B. Vargaftig, and N. Guiso. 1994. Characterization of murine lung inflammation after infection with parental *Bordetella pertussis* and mutants deficient in adhesins or toxins. Infection & Immunity 62, no. 7:2893-900.

43. Killeen, N., S. Sawada, and D. R. Littman. 1993. Regulated expression of human CD4 rescues helper T cell development in mice lacking expression of endogenous CD4. EMBO Journal 12, no. 4:1547-53.
44. Kitamura, D., J. Roes, R. Kuhn, and K. Rajewsky. 1991. A B cell-deficient mouse by targeted disruption of the membrane exon of the immunoglobulin mu chain gene. Nature 350, no. 6317:423-6.
45. Kyburz, D., P. Aichele, D. E. Speiser, H. Hengartner, R. M. Zinkemagel, and H. Pircher. 1993. T cell immunity after a viral infection versus T cell tolerance induced by soluble viral peptides. European Journal of Immunology 23, no. 8:1956-62.
46. Ladant D., Glaser P. and A. Ullmann. 1992. Insertional mutagenesis of *Bordetella pertussis* Adenylate cyclase. Journal of Biological Chemistry (4), no. 267: 2244-2250.
47. Ladant D., Calcium and membrane binding properties of bovine neurocalcin delta expressed in *Escherichia* cog, J Biol Chem 270 (1995) 3179-3185.
48. Ladant, D., and A. Ullmann. 1999. *Bordetella pertussis* adenylate cyclase: a toxin with multiple talents. Trends in Microbiology 7, no. 4:172-6.
49. Njamkepo, E., F. Pinot, D. Francois, N. Guiso, B. S. Polla, and M. Bachelet. 2000. Adaptive responses of human monocytes infected by *bordetella pertussis*: the role of adenylate cyclase hemolysin. J Cell Physiol 183, no. 1:91-9.
50. Otero, A. S., X. B. Yi, M. C. Gray, G. Szabo, and E. L. Hewlett. 1995. Membrane depolarization prevents cell invasion by *Bordetella pertussis* adenylate cyclase toxin. Journal of Biological Chemistry 270, no. 17:9695-9697.
51. Porgador, A., K. R. Irvine, A. Iwasaki, B. H. Barber, N. P. Restifo, and R. N. Germain. 1998. Predominant role for directly transfected dendritic cells in antigen presentation to CD8+ T cells after gene gun immunization. Journal of Experimental Medicine 188, no. 6:1075-82.
52. Pulendran, B., J. Lingappa, M. K. Kennedy, J. Smith, M. Teepe, A. Rudensky, C. R. Maliszewski, and E. Maraskovsky. 1997. Developmental pathways of dendritic cells in vivo: distinct function, phenotype, and localization of dendritic cell subsets in FLT3 ligand-treated mice. Journal of Immunology 159, no. 5:2222-31.
53. Reis e Sousa, C., and R. N. Germain. 1999. Analysis of adjuvant function by direct visualization of antigen presentation in vivo: endotoxin promotes accumulation of antigen-bearing dendritic cells in the T cell areas of lymphoid tissue. Journal of Immunology 162, no. 11:6552-61.1
54. Ridge, J. P., F. Di Rosa, and P. Matzinger. 1998. A conditioned dendritic cell can be a temporal bridge between a CD4+ T-helper and a T-killer cell. Nature 393, no. 6684:474-8.
55. Rogel, A., and E. Hanski. 1992. Distinct steps in the penetration of adenylate cyclase toxin of *Bordetella pertussis* into sheep erythrocytes. The Journal of Biological Chemistry 267, no. 31:22599-22605.
56. Rose, T., P. Sebo, J. Bellalou, and D. Ladant. 1995. Interaction of calcium with *Bordetella pertussisa* denylate cyclase toxin. Characterization of multiple calcium-binding sites and calcium-induced conformational changes. Journal of Biological Chemistry 270, no. 44:26370-6.
57. Sakamoto, H., J. Bellalou, P. Sebo, and D. Ladant. 1992. *Bordetella pertussis* adenylate cyclase toxin. Structural and functional independence of the catalytic and hemolytic activities. Journal of Biological Chemistry 267, no. 19:13598-602.
58. M. F. Saron, C. Fayolle, P. Sebo, D. Ladant, A. Ullmann and C. Leclerc. (1997) Anti-viral protection conferred by recombinant adenylate cyclase toxins from *Bordetella pertussis* carrying a CD8+ T-cell epitope from LCMV. Proc. Natl. Acad. Sci. USA, 94, 3314-3319
59. Schoenberger, S. P., R. E. Toes, E. I. van der Voort, R. Offring a, and C. J. Melief. 1998. T-cell help for cytotoxic T lymphocytes is mediated by CD40-CD40L interactions [see comments]. Nature 393, no. 6684:480-3.
60. Schuurhuis, D. H., S. Laban, R. E. Toes, P. Ricciardi-Castagnoli, M. J. Kleijmeer, E. I. van Der Voort, D. Rea, R. Offring a, H. J. Geuze, C. J. Melief, and F. Ossendorp. 2000. Immature dendritic cells acquire CD8(+) cytotoxic T lymphocyte priming capacity upon activation by T helper cell-independent or -dependent stimuli [In Process Citation]. J Exp Med 192, no. 1:145-50.
61. Sebo, P., Glaser, P., Sakamoto, H., and Ullmann, A. 1991. Gene 104, 19-24.
62. Viola, A., G. Iezzi, and A. Lanzavecchia. 1999. The role of dendritic cells in T cell priming: the importance of being professional. In Dendritic cells. T. L. Lotze and A. W. Thomson, editors. Academic Press, San Diego. 251-253.
63. Vremec, D., and K. Shortman. 1997. Dendritic cell subtypes in mouse lymphoid organs: cross-correlation of surface markers, changes with incubation, and differences among thymus, spleen, and lymph nodes. Journal of Immunology 159, no. 2:565-73.
64. Vremec, D., M. Zorbas, R. Scollay, D. J. Saunders, C. F. Ardavin, L. Wu, and K. Shortman. 1992. The surface phenotype of dendritic cells purified from mouse thymus and spleen: investigation of the CD8 expression by a subpopulation of dendritic cells. Journal of Experimental Medicine 176, no. 1:47-58.
65. Weiss, A. A., E. L. Hewlett, G. A. Myers, and S. Falkow. 1984. Pertussis toxin and extracytoplasmic adenylate cyclase as virulence factors of *Bordetella pertussis*. Journal of Infectious Diseases 150, no. 2:219-22
66. Weiss, A. A., and M. S. Goodwin. 1989. Lethal infection by *Bordetella pertussis* mutants in the infant mouse model. Infection & Immunity 57, no. 12:3757-64.
67. Wolff, J., G. H. Cook, A. R. Goldhammer, and S. A. Berkowitz. 1980. Calmodulin activates prokaryotic adenylate cyclase. Proceedings of the National Academy of Sciences of the United States of America 77, no. 7:3841-4.
68. Zhong, G., C. R. Sousa, and R. N. Germain. 1997. Antigen-unspecific B cells and lymphoid dendritic cells both show extensive surface expression of processed antigen-major histocompatibility complex class II complexes after soluble protein exposure in vivo or in vitro. Journal of Experimental Medicine 186, no. 5:673-82.
69. Zinkemagel, R. M., S. Ehl, P. Aichele, S. Oehen, T. Kundig, and H. Hengartner. 1997. Antigen localisation regulates immune responses in a dose- and time-dependent fashion: a geographical view of immune reactivity. Immunological Reviews 156:199-209.
70. WO 93/21324 (INSTITUT PASTEUR). Recombinant mutants for inducing specific immune response.

What is claimed is:

1. A proteinaceous vector comprising:
   a) a fragment of a *Bordetella* species adenylcyclase (CyaA) comprising amino acid residues 373-1706 and lacking all or part of residues 1-372; and
   b) a molecule of interest coupled to the CyaA fragment; wherein the proteinaceous vector binds to CD11b expressing dendritic cells such that the molecule of interest is delivered into the endocytic pathway of the CD11b-expressing cells.

2. The proteinaceous vector according to claim 1, wherein the *Bordetella* species adenylcyclase is a recombinant adenylcyclase.

3. The proteinaceous vector according to claim 1, wherein the *Bordetella* species is *Bordetella pertussis*.

4. The proteinaceous vector according to claim 1, wherein the *Bordetella* species adenylcyclase (CyaA) fragment is the *Bordetella pertussis* adenylcyclase (CyaA) lacking residues 1-372.

5. The proteinaceous vector according to claim 1, wherein the molecule of interest is genetically coupled to the adenylcyclase (CyaA) fragment.

6. The proteinaceous vector according to claim 1, wherein the molecule of interest is chemically coupled to the adenylcyclase (CyaA) fragment.

7. The proteinaceous vector according to claim 1, wherein the *Bordetella* species adenylcyclase (CyaA) fragment has been genetically detoxified.

8. The proteinaceous vector according to claim 1, wherein the molecule of interest comprises a peptide antigen.

9. The proteinaceous vector according to claim 8, wherein the proteinaceous vector binds to CD11 b expressing dendritic cells such that the peptide antigen is translocated to the cytosolic pathway for MHC class I presentation.

10. The proteinaceous vector according to claim 9, wherein administration of the proteinaceous vector to a subject induces a cytotoxic T lymphocyte (CTL) response against the peptide antigen.

11. The proteinaceous vector according to claim 10, wherein the CTL response is a CD8+ response.

12. The proteinaceous vector according to claim 10, wherein the CTL response is a CD4+ response.

13. A pharmaceutical composition comprising the proteinaceous vector of claim 1 and a pharmaceutically acceptable carrier.

14. An immunogenic composition comprising the pharmaceutical composition of claim 13.

15. The immunogenic composition of claim 14, wherein the immunogenic composition does not contain an adjuvant.

16. A CD11b-expressing cell bound to the proteinaceous vector of claim 1.

* * * * *

SEQUENCE LISTING

<160> NUMBER OF SEQ ID NOS: 11

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: PEPTIDE
<222> LOCATION: (1)..(14)
<223> OTHER INFORMATION: ovalbumin epitope

<400> SEQUENCE: 1

Ala Ser Cys Gly Ser Ile Ile Asn Phe Glu Lys Leu Gly Thr
 1               5                   10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: PEPTIDE
<222> LOCATION: (1)..(8)
<223> OTHER INFORMATION: pOVA synthetic peptide

<400> SEQUENCE: 2

Ser Ile Ile Asn Phe Glu Lys Leu
 1               5

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: PEPTIDE
<222> LOCATION: (1)..(15)
<223> OTHER INFORMATION: CMVgp epitope

<400> SEQUENCE: 3

Pro Ala Ser Ala Lys Ala Val Tyr Asn Phe Ala Thr Cys Gly Thr
 1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: PEPTIDE
<222> LOCATION: (1)..(12)
<223> OTHER INFORMATION: CEA 571 epitope

<400> SEQUENCE: 4

Cys Gly Gly Tyr Leu Ser Gly Ala Asn Leu Asn Leu
 1               5                   10

<210> SEQ ID NO 5
<211> LENGTH: 12
<212> TYPE: PRT
<213> ORGANISM: Artificial Sequence

```
<220> FEATURE:
<223> OTHER INFORMATION: Description of Artificial Sequence: synthetic
      peptide
<220> FEATURE:
<221> NAME/KEY: PEPTIDE
<222> LOCATION: (1)..(12)
<223> OTHER INFORMATION: Gp100 epitope

<400> SEQUENCE: 5

Cys Gly Gly Ile Thr Asp Gln Val Pro Phe Ser Val
  1               5                  10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: PEPTIDE
<222> LOCATION: (1)..(13)
<223> OTHER INFORMATION: MelanA epitope

<400> SEQUENCE: 6

Cys Gly Gly Glu Ala Ala Gly Ile Gly Ile Leu Thr Val
  1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: PEPTIDE
<222> LOCATION: (1)..(12)
<223> OTHER INFORMATION: Tyrosinase epitope

<400> SEQUENCE: 7

Cys Gly Gly Tyr Met Asp Gly Thr Met Ser Gln Val
  1               5                  10

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: intergenic
      region
<220> FEATURE:
<221> NAME/KEY: CDS
<222> LOCATION: (1)..(15)
<223> OTHER INFORMATION: C-terminus extension of CyaC
<220> FEATURE:
<221> NAME/KEY: CDS
<222> LOCATION: (22)..(45)
<223> OTHER INFORMATION: First codons of CyaA 373-1706

<400> SEQUENCE: 8 cgg aat aag gag gaa taacat atg ggc tgc ggg aat tcg aag ttc          45
Arg Asn Lys Glu Glu         Met Gly Cys Gly Asn Ser Lys Phe
  1               5                         10

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: intergenic
``` region

<400> SEQUENCE: 9

Arg Asn Lys Glu Glu
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: intergenic
      region

<400> SEQUENCE: 10

Met Gly Cys Gly Asn Ser Lys Phe
 1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: PEPTIDE
<222> LOCATION: (1)..(16)
<223> OTHER INFORMATION: OVA epitope

<400> SEQUENCE: 11

Arg Ala Ser Cys Gly Ser Ile Ile Asn Phe Glu Lys Leu Gly Thr Ala
 1               5                  10                  15